US006951871B2

(12) United States Patent
Aslanian et al.

(10) Patent No.: US 6,951,871 B2
(45) Date of Patent: Oct. 4, 2005

(54) INDOLE DERIVATIVES USEFUL AS HISTAMINE $H_3$ ANTAGONISTS

(75) Inventors: Robert G. Aslanian, Rockaway, NJ (US); Michael Y. Berlin, Flemington, NJ (US); Pietro Mangiaracina, Monsey, NY (US); Kevin D. McCormick, Edison, NJ (US); Mwangi W. Mutahi, Orange, NJ (US); Stuart B. Rosenblum, West Orange, NJ (US)

(73) Assignee: Schering Corporation, Kenilworth, NJ (US)

( * ) Notice: Subject to any disclaimer, the term of this patent is extended or adjusted under 35 U.S.C. 154(b) by 15 days.

(21) Appl. No.: 10/600,674

(22) Filed: Jun. 20, 2003

(65) Prior Publication Data

US 2004/0019099 A1 Jan. 29, 2004

Related U.S. Application Data

(60) Provisional application No. 60/390,987, filed on Jun. 24, 2002.

(51) Int. Cl.$^7$ ............... A61K 31/445; C07D 401/04; C07D 401/14
(52) U.S. Cl. .................. 514/316; 514/300; 546/113; 546/187
(58) Field of Search ............... 514/300, 316; 546/113, 187

(56) References Cited

U.S. PATENT DOCUMENTS

| 5,217,986 | A | * | 6/1993 | Pomponi et al. | 514/400 |
|---|---|---|---|---|---|
| 5,352,707 | A | * | 10/1994 | Pompni et al. | 514/651 |
| 5,846,982 | A | | 12/1998 | Audia et al. | 514/318 |
| 5,869,479 | A | | 2/1999 | Kreutner et al. | 514/212 |
| 6,162,818 | A | * | 12/2000 | Henry et al. | 514/397 |

FOREIGN PATENT DOCUMENTS

| EP | 0 470 039 | 12/1994 |
|---|---|---|
| JP | 63-227573 | 9/1988 |
| WO | WO 98/06394 | 2/1998 |
| WO | WO 01/46181 | 6/2001 |
| WO | WO 02/32893 | 4/2002 |
| WO | 02/36589 | 5/2002 |
| WO | 02/072093 | 9/2002 |
| WO | WO 02/072570 | 9/2002 |

OTHER PUBLICATIONS

McLeod et al. "Histamine H3 antagonists" CA 136:48247 (2001).*
Terzioglu et al. Synthesis and structure–activity relationships . . . Bioorganic Med. Chem. Lett. vol. 14, p.5251–56 (2004).*
Baker Bott "In print reach–through claims" Attorneys practice profiles news and events (2002).*
Rizzo et al., *European Journal of Pharmacology*, vol. 294 (1995) pp. 329–335.
G. Heinisch et al., *Monatshefte fur Chemie*, vol. 104 (1973) pp. 1372–1382.
Obase et al., *J. Heterocyclic Chemistry*, vol. 20 (1983) pp. 565–573.
U.S. Appl. No. 10/417,391 pp. 1–127.
U.S. Appl. No. 10/414,943 pp. 1–87.

* cited by examiner

*Primary Examiner*—Celia Chang
(74) *Attorney, Agent, or Firm*—Anita W. Magatti

(57) ABSTRACT

Disclosed are novel compounds of the formula

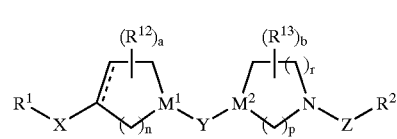

wherein $M^1$ is CH or N and $M^2$ is $C(R^3)$ or N; $R^1$ is optionally substituted indolyl or an aza derivative thereof; $R^2$ is optionally substituted aryl or heteroaryl; and the remaining variables are as defined in the specification.

Also disclosed are pharmaceutical compositions comprising the compounds of formula I.

Also disclosed are methods of treating various diseases or conditions, such as, for example, allergy, allergy-induced airway responses, and congestion (e.g., nasal congestion) using the compounds of Formula I.

Also disclosed are methods of treating various diseases or conditions, such as, for example, allergy, allergy-induced airway responses, and congestion (e.g., nasal congestion) using the compounds of formula I in combination with a $H_1$ receptor antagonist.

17 Claims, No Drawings

INDOLE DERIVATIVES USEFUL AS HISTAMINE $H_3$ ANTAGONISTS

CROSS REFERENCE TO RELATED APPLICATIONS

This application claims the benefit of U.S. Provisional Application No. 60/390,987, filed Jun. 24, 2002.

FIELD OF THE INVENTION

The present invention relates to novel substituted indoles and derivatives thereof, useful as histamine $H_3$ antagonists. The invention also relates to pharmaceutical compositions comprising said compounds and their use in treating inflammatory diseases, allergic conditions and central nervous system disorders. The invention also relates to the use of a combination of novel histamine $H_3$ antagonists of this invention with histamine $H_1$ compounds for the treatment of inflammatory diseases and allergic conditions, as well as pharmaceutical compositions comprising a combination of one or more novel histamine $H_3$ antagonist compounds of the invention with one or more histamine $H_1$ compounds.

BACKGROUND OF THE INVENTION

The histamine receptors, $H_1$, $H_2$ and $H_3$ are well-identified forms. The $H_1$ receptors are those that mediate the response antagonized by conventional antihistamines. $H_1$ receptors are present, for example, in the ileum, the skin, and the bronchial smooth muscle of humans and other mammals. Through $H_2$ receptor-mediated responses, histamine stimulates gastric acid secretion in mammals and the chronotropic effect in isolated mammalian atria.

$H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates nonepinephrine outflow to resistance and capacitance vessels, causing vasodilation.

Imidazole $H_3$ receptor antagonists are well known in the art. More recently, non-imidazole $H_3$ receptor antagonists have been disclosed in PCT US01/32151, filed Oct. 15, 2001, and U.S. application Ser. No. 10/095,134, filed Mar. 11, 2002.

U.S. Pat. No. 5,869,479 discloses compositions for the treatment of the symptoms of allergic rhinitis using a combination of at least one histamine $H_1$ receptor antagonist and at least one histamine $H_3$ receptor antagonist.

SUMMARY OF THE INVENTION

The present invention provides novel compounds of formula I:

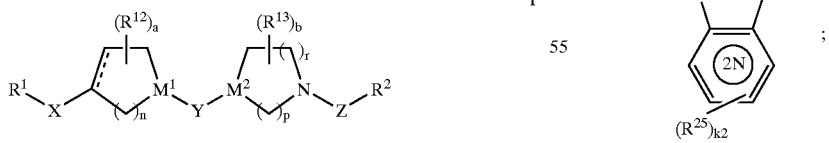

or a pharmaceutically acceptable salt or solvate thereof, wherein:
a is 0 to 3;
b is 0 to 3;
n is 1, 2 or 3;
p is 1, 2 or 3;
r is 0, 1, 2, or 3;
X is a bond or $C_1$–$C_6$ alkylene;

$M^1$ is CH or N;
$M^2$ is $C(R^3)$ or N;
with the provisos that when $M^2$ is N, p is not 1; and that when r is 0, $M^2$ is $C(R^3)$; and that the sum of p and r is 1 to 4;
Y is —C(=O)—, —C(=S)—, —(CH$_2$)$_q$—, —NR$^4$C(=O)—, —C(=O)NR$^4$—, —C(=O)CH$_2$—, SO$_{1-2}$—, —C(=N—CN)—NH— or —NH—C(=N—CN)—; with the provisos that when $M^1$ is N, Y is not —NR$^4$C(=O)— or —NH—C(=N—CN)—; and when $M^2$ is N, Y is not —C(=O)NR$^4$— or —C(=N—CN)—NH—;
q is 1 to 5, provided that when $M^1$ and $M^2$ are both N, q is not 1;
Z is a bond, $C_1$–$C_6$ alkylene, $C_2$–$C_6$ alkenylene, —C(=O)—, —CH(CN)— or —CH$_2$C(=O)NR$^4$—;
$R^1$ is

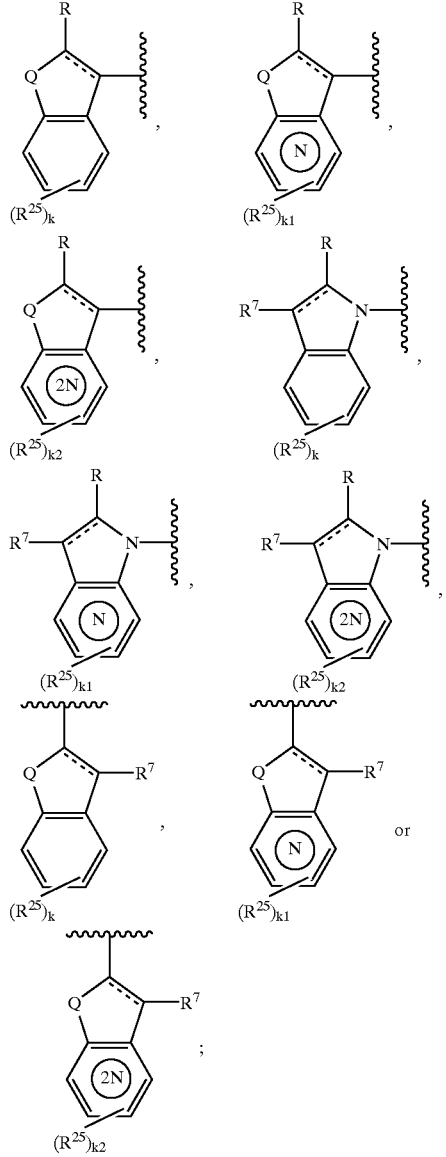

Q is —N(R$^8$)—, —S— or —O—;
k is 0, 1, 2, 3 or 4;
k1 is 0, 1, 2, or 3;
k2 is 0, 1 or 2;

the dotted line represents an optional double bond;
R and R$^7$ are independently selected from the group consisting of H, $C_1$–$C_6$ alkyl, halo($C_1$–$C_6$)alkyl-, $C_1$–$C_6$ alkoxy, $(C_1-C_6)$alkoxy-$(C_1-C_6)$alkyl-, $(C_1-C_6)$-alkoxy-$(C_1-C_6)$alkoxy, $(C_1-C_6)$alkoxy-$(C_1-C_6)$alkyl-$SO_{0-2}$, $R^{32}$-aryl $(C_1-C_6)$alkoxy-, $R^{32}$-aryl-$(C_1-C_6)$alkyl-, $R^{32}$-aryl, $R^{32}$-aryloxy, $R^{32}$-heteroaryl, $(C_3-C_6)$cycloalkyl, $(C_3-C_6)$cycloalkyl-$(C_1-C_6)$alkyl, $(C_3-C_6)$cycloalkyl-$(C_1-C_6)$alkoxy, $(C_3-C_6)$cycloalkyl-oxy-, $R^{37}$-heterocyclo-alkyl, $N(R^{30})(R^{31})$—$(C_1-C_6)$alkyl-, —$N(R^{30})(R^{31})$, —NH—$(C_1-C_6)$alkyl-O—$(C_1-C_6)$alkyl, —NHC(O)NH$(R^{29})$; $R^{22}$—S(O)$_{0-2}$—, halo$(C_1-C_6)$alkyl-S(O)$_{0-2}$—, $N(R^{30})(R^{31})$—$(C_1-C_6)$alkyl-S(O)$_{0-2}$—, benzoyl, $(C_1-C_6)$alkoxy-carbonyl, $R^{37}$-heterocycloalkyl-N$(R^{29})$—C(O)—, $(C_1-C_6)$alkyl-N$(R^{29})$—C(O)—, $(C_1-C_6)$alkyl-N$(C_1-C_6$ alkoxy)-C(O)—, —C(=NOR$^{36}$)R$^{36}$ and —NHC(O)R$^{29}$; and when the optional double bond is not present, $R^7$ can be OH;

$R^8$ is H, $C_1-C_6$ alkyl, halo$(C_1-C_6)$alkyl-, $(C_1-C_6)$alkoxy-$(C_2-C_6)$alkyl-, $R^{32}$-aryl$(C_1-C_6)$alkyl-, $R^{32}$-aryl, $R^{32}$-heteroaryl, $R^{32}$-heteroaryl$(C_1-C_6)$alkyl-, $(C_3-C_6)$cycloalkyl, $(C_3-C_6)$cycloalkyl-$(C_1-C_6)$alkyl, $R^{37}$-heterocycloalkyl, $R^{37}$-heterocycloalkyl$(C_1-C_6)$alkyl, $N(R^{30})(R^{31})$—$(C_2-C_6)$alkyl-, $R^{22}$—S(O)$_2$—, halo$(C_1-C_6)$alkyl-S(O)$_2$—, $R^{22}$—S(O)$_{0-1}$—$(C_2-C_6)$alkyl-, halo$(C_1-C_6)$alkyl-S(O)$_{0-1}$—$(C_2-C_6)$alkyl-, $(C_1-C_6)$alkyl-N$(R^{29})$—SO$_2$—, or $R^{32}$-heteroaryl-SO$_2$;

$R^2$ is a six-membered heteroaryl ring having 1 or 2 heteroatoms independently selected from N or N—O, with the remaining ring atoms being carbon; a five-membered heteroaryl ring having 1, 2, 3 or 4 heteroatoms independently selected from N, O or S, with the remaining ring atoms being carbon; $R^{32}$-quinolyl; $R^{32}$-aryl;

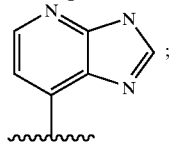

or heterocycloalkyl; wherein said six-membered heteroaryl ring or said five-membered heteroaryl ring is optionally substituted by $R^6$;

$R^3$ is H, halogen, $C_1-C_6$ alkyl, —OH or $(C_1-C_6)$alkoxy;

$R^4$ is independently selected from the group consisting of hydrogen, $C_1-C_6$ alkyl, $C_3-C_6$ cycloalkyl, $(C_3-C_6)$cycloalkyl$(C_1-C_6)$alkyl, $R^{33}$-aryl, $R^{33}$-aryl$(C_1-C_6)$alkyl, and $R^{32}$-heteroaryl;

$R^5$ is hydrogen, $C_1-C_6$ alkyl, —C(O)R$^{20}$, —C(O)$_2$R$^{20}$, —C(O)N(R$^{20}$)$_2$, $R^{33}$-aryl$(C_1-C_6)$alkyl or $(C_1-C_6)$alkyl-SO$_2$—;

$R^6$ is 1 to 3 substituents independently selected from the group consisting of —OH, halogen, $C_1-C_6$ alkyl, $C_1-C_6$ alkoxy, —CF$_3$, —NR$^4$R$^5$, —$(C_1-C_6)$alkyl-NR$^4$R$^5$, phenyl, $R^{33}$-phenyl, NO$_2$, —CO$_2$R$^4$, —CON(R$^4$)$_2$, —NHC(O)N(R$^4$)$_2$, $R^{32}$-heteroaryl-SO$_2$—NH—, $R^{32}$-aryl-$(C_1-C_6)$alkyl-NH—, $R^{32}$-heteroaryl-$(C_1-C_6)$alkyl-NH—, $R^{32}$-heteroaryl-NH—C(O)—NH—, $R^{37}$-heterocycloalkyl-N(R$^{29}$)—C(O)— and $R^{37}$-heterocycloalkyl-N(R$^{29}$)—C(O)—NH—;

$R^{12}$ is independently selected from the group consisting of $C_1-C_6$ alkyl, hydroxyl, $C_1-C_6$ alkoxy, or fluoro, provided that when $R^{12}$ is hydroxy or fluoro, then $R^{12}$ is not bound to a carbon adjacent to a nitrogen; or $R^{12}$ forms a $C_1$ to $C_2$ alkyl bridge from one ring carbon to another ring carbon;

$R^{13}$ is independently selected from the group consisting of $C_1-C_6$ alkyl, hydroxyl, $C_1-C_6$ alkoxy, or fluoro, provided that when $R^{13}$ is hydroxy or fluoro then $R^{13}$ is not bound to a carbon adjacent to a nitrogen; or forms a $C_1$ to $C_2$ alkyl bridge from one ring carbon to another ring carbon; or $R^{13}$ is =O;

$R^{20}$ is independently selected from the group consisting of hydrogen, $C_1-C_6$ alkyl, or aryl, wherein said aryl group is optionally substituted with from 1 to 3 groups independently selected from halogen, —CF$_3$, —OCF$_3$, hydroxyl, or methoxy; or when two $R^{20}$ groups are present, said two $R^{20}$ groups taken together with the nitrogen to which they are bound can form a five or six membered heterocyclic ring;

$R^{22}$ is $C_1-C_6$ alkyl, $R^{34}$-aryl or heterocycloalkyl;

$R^{24}$ is H, $C_1-C_6$ alkyl, —SO$_2$R$^{22}$ or $R^{34}$-aryl;

$R^{25}$ is independently selected from the group consisting of $C_1-C_6$ alkyl, halogen, CN, —CF$_3$, —OH, $C_1-C_6$ alkoxy, $(C_1-C_6)$alkyl-C(O)—, aryl-C(O)—, N(R$^4$)(R$^5$)—C(O)—, N(R$^4$)(R$^5$)—S(O)$_{1-2}$—, halo-$(C_1-C_6)$alkyl- or halo-$(C_1-C_6)$alkoxy-$(C_1-C_6)$alkyl-;

$R^{29}$ is H, $C_1-C_6$ alkyl, $R^{35}$-aryl or $R^{35}$-aryl$(C_1-C_6)$alkyl-;

$R^{30}$ is H, $C_1-C_6$ alkyl-, $R^{35}$-aryl or $R^{35}$-aryl$(C_1-C_6)$alkyl-;

$R^{31}$ is H, $C_1-C_6$ alkyl, $R^{35}$-aryl, $R^{35}$-aryl$(C_1-C_6)$alkyl-, $(C_1-C_6)$alkyl-C(O)—, $R^{35}$-aryl-C(O)—, N(R$^4$)(R$^5$)—C(O)—, $(C_1-C_6)$alkyl-S(O)$_2$— or $R^{35}$-aryl-S(O)$_2$—;

or $R^{30}$ and $R^{31}$ together are —(CH$_2$)$_{4-5}$—, —(CH$_2$)$_2$—O—(CH$_2$)$_2$— or —(CH$_2$)$_2$—N(R$^{29}$)—(CH$_2$)$_2$— and form a ring with the nitrogen to which they are attached;

$R^{32}$ is 1 to 3 substituents independently selected from the group consisting of H, —OH, halogen, $C_1-C_6$ alkyl, $C_1-C_6$ alkoxy, $R^{35}$-aryl-O—, —SR$^{22}$, —CF$_3$, —OCF$_3$, —OCHF$_2$, —NR$^4$R$^5$, phenyl, $R^{33}$-phenyl, —NO$_2$, —CO$_2$R$^4$, —CON(R$^4$)$_2$, —S(O)$_2$R$^{22}$, —S(O)$_2$N(R$^{20}$)$_2$, —N(R$^{24}$)S(O)$_2$R$^{22}$, —CN, hydroxy-$(C_1-C_6)$alkyl-, —OCH$_2$CH$_2$OR$^{22}$, and $R^{35}$-aryl$(C_1-C_6)$alkyl-O—, wherein said aryl group is optionally substituted with 1 to 3 independently selected halogens;

$R^{33}$ is 1 to 3 substituents independently selected from the group consisting of $C_1-C_6$ alkyl, halogen, —CN, —NO$_2$, —OCHF$_2$ and —O—$(C_1-C_6)$alkyl;

$R^{34}$ is 1 to 3 substituents independently selected from the group consisting of H, halogen, —CF$_3$, —OCF$_3$, —OH and —OCH$_3$.

$R^{35}$ is 1 to 3 substituents independently selected from the group consisting of hydrogen, halo, $C_1-C_6$ alkyl, hydroxy, $C_1-C_6$ alkoxy, phenoxy, —CF$_3$, —N(R$^{36}$)$_2$, —COOR$^{20}$ and —NO$_2$;

$R^{36}$ is independently selected from the group consisting of H and $C_1-C_6$ alkyl; and $R^{37}$ is independently selected from the group consisting of H, $C_1-C_6$ alkyl and $(C_1-C_6)$alkoxycarbonyl.

This invention also provides a pharmaceutical composition comprising an effective amount of at least one compound of formula I and a pharmaceutically acceptable carrier.

This invention further provides a method of treating: allergy, allergy-induced airway (e.g., upper airway) responses, congestion (e.g., nasal congestion), hypotension, cardiovascular disease, diseases of the GI tract, hyper- and hypo-motility and acidic secretion of the gastro-intestinal tract, obesity, sleeping disorders (e.g., hypersomnia, somnolence, and narcolepsy), disturbances of the central nervous system, attention deficit hyperactivity disorder (ADHD), hypo- and hyperactivity of the central nervous system (for example, agitation and depression), and/or other CNS disorders (such as Alzheimer's, schizophrenia, and migraine) comprising administering to a patient in need of such treatment an effective amount of at least one compound of formula I. "Patient" means a mammal, typically a human, although veterinary use is also contemplated.

Compounds of this invention are particularly useful for treating allergy, allergy-induced airway responses and/or congestion.

This invention further provides a pharmaceutical composition comprising an effective amount of a combination of at least one compound of formula I and at least one $H_1$ receptor antagonist in combination with a pharmaceutically acceptable carrier.

This invention further provides a method of treating allergy, allergy-induced airway (e.g., upper airway) responses, and/or congestion (e.g., nasal congestion) comprising administering to a patient in need of such treatment (e.g., a mammal, such as a human being) an effective amount of a combination of at least one compound of formula I and at least one $H_1$ receptor antagonist.

Kits comprising a compound of formula I in a pharmaceutical composition, and a separate $H_1$ receptor antagonist in a pharmaceutical composition in a single package are also contemplated.

DETAILED DESCRIPTION OF THE INVENTION

Preferred definitions of the variables in the structure of formula I are as follows:

$R^1$ is preferably 3-indolyl or 1-indolyl. The double bond is preferably present in the $R^1$ substituent.

R is preferably H, alkyl, $R^{32}$-aryl, $R^{32}$-heteroaryl, $(C_1–C_6)$ alkoxy-carbonyl or $(C_1–C_6)$alkyl-N($R^{29}$)—C(O)—. When R is $(C_1–C_6)$alkyl-N($R^{29}$)—C(O)—, $R^{29}$ is preferably H or $C_1–C_6$ alkyl. More preferably, R is $R^{32}$-aryl or $R^{32}$-heteroaryl. Especially preferred are $R^{32}$-phenyl and $R^{32}$-pyridyl. $R^7$ is preferably H.

$R^8$ is preferably H, $R^{32}$-aryl($C_1–C_6$)alkyl-, $R^{32}$-heteroaryl $(C_1–C_6)$alkyl-, $R^{32}$-aryl, $R^{32}$-heteroaryl, $(C_1–C_6)$alkyl-N $(R^{29})$—$SO_2$— or $R^{37}$-heterocycloalkyl($C_1–C_6$)alkyl-. Especially preferred are H, $R^{32}$-benzyl, $R^{32}$-pyridylmethyl, $(C_1–C_6)$alkyl-N($R^{29}$)—$SO_2$— wherein $R^{29}$ is H or $C_1–C_6$ alkyl, and piperidinoethyl.

$R^{25}$ is preferably H, halogen or —$CF_3$ and k is 0 or 1. When $R^1$ is an aza- or diaza derivative of indole, R is preferably as defined above, and $k_1$ and $k_2$ are preferably zero.

X is preferably a bond.

$R^2$ is preferably a six-membered heteroaryl ring, optionally substituted with one substituent. More preferably, $R^2$ is pyridyl, pyrimidyl or pyridazinyl, optionally substituted with —$NH_2$.

Y is preferably —C(O)—.

Z is preferably straight or branched $C_1–C_3$ alkyl. Methylene is an especially preferred Z group.

$M^1$ is preferably N; a is preferably 0; and n is preferably 2; the optional double bond in the ring containing $M^1$ is preferably not present (i.e., a single bond is present).

$M^2$ is preferably C($R^3$) wherein $R^3$ is hydrogen or fluoro; b is preferably 0; r is preferably 1; and p is preferably 2.

As used herein, the following terms have the following meanings, unless indicated otherwise:

alkyl (including, for example, the alkyl portions of arylalkyl and alkoxy) represents straight and branched carbon chains and contains from one to six carbon atoms;

alkylene represents a divalent straight or branched alkyl chain, e.g., ethylene (—$CH_2$—) or propylene (—$CH_2CH_2CH_2$—);

haloalkyl or haloalkoxy represent alkyl or alkoxy chains as defined above wherein one or more hydrogen atoms are replaced by halogen atoms, e.g., —$CF_3$, $CF_3CH_2CH_2$—, $CF_3CF_2$— or $CF_3O$—;

aryl (including the aryl portion of arylalkyl) represents a carbocyclic group containing from 6 to 15 carbon atoms and having at least one aromatic ring (e.g., aryl is a phenyl or naphthyl ring), with all available substitutable carbon atoms of the carbocyclic group being intended as possible points of attachment;

arylalkyl represents an aryl group, as defined above, bound to an alkyl group, as defined above, wherein said alkyl group is bound to the compound;

cycloalkyl represents saturated carbocyclic rings of from 3 to 6 carbon atoms;

halogen (halo) represents fluoro, chloro, bromo and iodo;

heteroaryl represents cyclic groups, having 1 to 4 heteroatoms selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms. The rings do not contain adjacent oxygen and/or sulfur atoms. Examples include but are not limited to isothiazolyl, isoxazolyl, oxazolyl, furazanyl, triazolyl, tetrazolyl, thiazolyl, thienyl, furanyl (furyl), pyrrolyl, pyrazolyl, pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide), triazinyl, pteridinyl, indolyl (benzopyrrolyl), pyridopyrazinyl, isoquinolinyl, quinolinyl, naphthyridinyl; the 5- and 6-membered heteroaryl groups included in the definition of $R^2$ are exemplified by the heteroaryl groups listed above; all available substitutable carbon and nitrogen atoms can be substituted as defined.

heterocycloalkyl represents a saturated, carbocylic ring containing from 3 to 15 carbon atoms, preferably from 4 to 6 carbon atoms, which carbocyclic ring is interrupted by 1 to 3 hetero atoms selected from —O—, —S—, —$SO$—, —$SO_2$ or —$NR^{40}$— wherein $R^{40}$ represents H, $C_1$ to $C_6$ alkyl, arylalkyl, —C(O)$R^{20}$, —C(O)O$R^{20}$, or —C(O)N $(R^{20})_2$ (wherein each $R^{20}$ is independently selected); examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl.

Ⓝ, for example in the structure

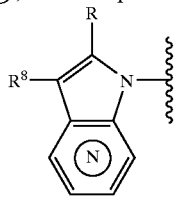

represents a nitrogen atom that is located at one of the 4 non-fused positions of the ring, i.e., positions 4, 5, 6 or 7 indicated below:

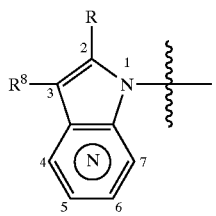

Similarly,

means that two nitrogen atoms are located at any two of the 4 non-fused positions of the ring, e.g., the 4 and 6 positions, the 4 and 7 positions, or the 5 and 6 positions.

A dotted line in the structure of formula I or in the structures defining $R^1$ indicates an option double bond. The presence or absence of a double bond in the structure of formula I is independent of the presence or absence of a double bond in the $R^1$ substituent.

Also, as used herein, "upper airway" usually means the upper respiratory system—i.e., the nose, throat, and associated structures.

Also, as used herein, "effective amount" generally means a therapeutically effective amount.

A line drawn into a ring means that the indicated bond may be attached to any of the substitutable ring carbon atoms.

Certain compounds of the invention may exist in different isomeric (e.g., enantiomers, diastereoisomers and geometric) forms. The invention contemplates all such isomers both in pure form and in admixture, including racemic mixtures. Enol forms and tautomers are also included.

The compounds of this invention are ligands for the histamine $H_3$ receptor. The compounds of this invention can also be described as antagonists of the $H_3$ receptor, or as $H_3$ antagonists.

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms can differ from their corresponding salt forms somewhat in certain physical properties, such as solubility in polar solvents, but the salts are otherwise equivalent to their corresponding free base forms for purposes of this invention.

Depending upon the substituents on the inventive compounds, one may be able to form salts with bases. Thus, for example, if there is a carboxylic acid substituent in the molecule, a salt may be formed with an inorganic as well as organic base such as, for example, NaOH, KOH, $NH_4OH$, tetraalkylammonium hydroxide, and the like.

The compounds of formula I can exist in unsolvated as well as solvated forms, including hydrated forms, e.g., hemi-hydrate. In general, the solvated form, with pharmaceutically acceptable solvents such as water, ethanol and the like are equivalent to the unsolvated form for purposes of the invention.

The compounds of this invention can be combined with an $H_1$ receptor antagonist (i.e., the compounds of this invention can be combined with an $H_1$ receptor antagonist in a pharmaceutical composition, or the compounds of this invention can be administered with an $H_1$ receptor antagonist).

Numerous chemical substances are known to have histamine $H_1$ receptor antagonist activity and can therefore be used in the methods of this invention. Many $H_1$ receptor antagonists useful in the methods of this invention can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

More preferably, said $H_1$ receptor antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

Most preferably, said $H_1$ receptor antagonist is selected from: azatadine, brompheniramine, cetirizine, chlorpheniramine, carebastine, descarboethoxy-loratadine, diphenhydramine, ebastine, fexofenadine, loratadine, or norastemizole.

Even more preferably, said $H_1$ antagonist is selected from loratadine, descarboethoxyloratadine, fexofenadine or cetirizine. Still even more preferably, said $H_1$ antagonist is loratadine or descarboethoxyloratadine.

In one preferred embodiment, said $H_1$ receptor antagonist is loratadine.

In another preferred embodiment, said $H_1$ receptor antagonist is descarboethoxyloratadine.

In still another preferred embodiment, said $H_1$ receptor antagonist is fexofenadine.

In yet another preferred embodiment, said $H_1$ receptor antagonist is cetirizine.

Preferably, in the above methods, allergy-induced airway responses are treated.

Also, preferably, in the above methods, allergy is treated.

Also, preferably, in the above methods, nasal congestion is treated.

In the methods of this invention wherein a combination of an $H_3$ antagonist of this invention (compound of formula I) is administered with an $H_1$ antagonist, the antagonists can be administered simultaneously or sequentially (first one and then the other over a period of time). In general, when the antagonists are administered sequentially, the $H_3$ antagonist of this invention (compound of formula I) is administered first.

The preparation of compounds of Formula I can be realized in many ways known to those skilled in the art. Following are typical procedures for preparing various compounds; other procedures may also be applicable and the procedures may be modified to prepare other compounds within the scope of Formula I. One skilled in the art will recognize that one route will be optimal depending on the choice of appendage substituents. Additionally, one skilled in the art will recognize that in some cases the order of steps has to be controlled to avoid functional group incompatibilities.

The structure of formula I can be considered to be made up of four parts, A, B, C and D, as shown below:

I

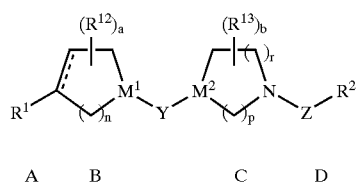

A   B    C   D

One possible route for preparing compounds of formula I involves a linear sequence of reactions to obtain the desired compounds, i.e.,

A+B→AB+C→ABC+D→ABCD

The synthesis using this approach is given below for compounds in which $R^1$ is 3-indolyl, $M^1$ is N, $M^2$ is CH, and Y is —C(O)—:

A + B → AB

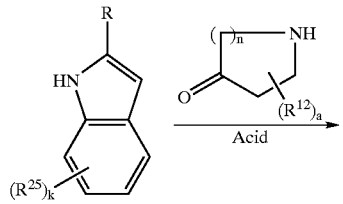

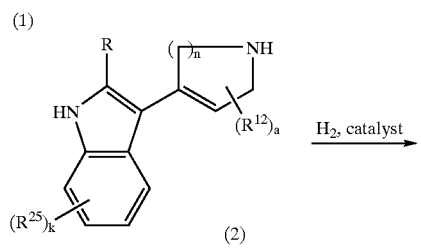

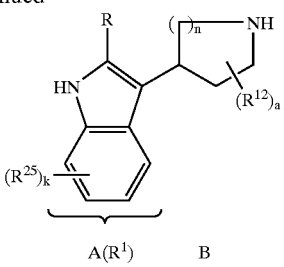

A($R^1$)        B

Indole (1), obtained commercially or through procedures well known in the art, is reacted under acidic conditions such as acetic acid and phosphoric acid or the like at a temperature of 20°–100° C. with a ketone for a time sufficient to complete the reaction to give compound (2). Compound (2) can be reduced using a metal catalyst such as palladium, platinum or the like in a solvent such as methanol, ethanol, ethyl acetate or the like at a temperature from 20°–50° C. under an atmosphere of hydrogen or in the presence of a hydrogen source such as $NH_4Cl$ or $NH_4HCO_2$ to give the fragment AB. Other AB ring analogs can be prepared using procedures well known to those versed in the art, see for example J. Heterocyclic Chem., 30, (1993), 445, U.S. Pat. No. 5,846,982, WO 01/46181, and EP 470039.

AB + C → ABC

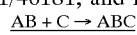

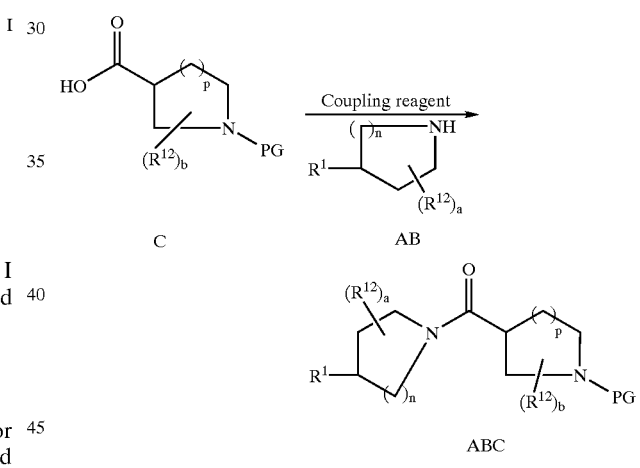

Amine AB can be coupled to acid C, wherein PG is a protecting group, using a number of methods well known in the art such as using EDC, DCC or PyBOP (benzotriazole-1-yl-oxy-trispyrrolidino-phosphonium hexaflurophosphate). Alternatively, the acid C can be activated by conversion to the acid chloride or mixed anhydride and then reacted with the amine AB to give ABC. Suitable protecting groups for C include t-BOC or the like.

ABC + D → ABCD

Step 1

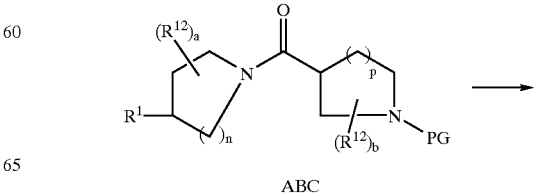

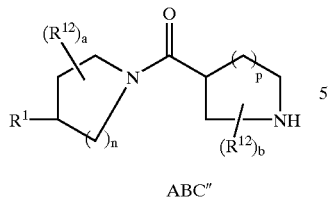

ABC''

Compound ABC is deprotected using conditions suitable for the removal of the protecting group, PG, to give ABC''.

Step 2

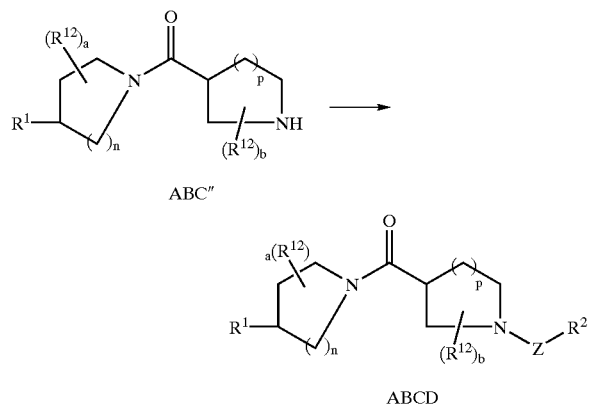

For compounds wherein $Z\text{-}R^2 = -(CH_2)_{1-6} - R^2$, ABC'' can be reacted with an aldehyde of the formula $R^2(CH_2)_{1-5}CHO$ in the presence of a reducing agent such as $NaBH_4$, $NaBH(OAc)_3$ or the like, in a suitable solvent such as methanol, ethanol, dichloromethane or the like, to give ABCD. Alternatively, ABC can be reacted with an alkylating agent $R^2-(CH_2)-X$, in which X is a leaving group such as a halogen or mesylate or the like, in a solvent such as DMSO, DMF or the like, in the presence of a base, to give ABCD.

For compounds wherein $Z\text{-}R^2 = C(O) - R^2$, ABC'' can be coupled with an acid $R^2CO_2H$ in the presence of a coupling agent such as EDC, DCC or PyBOP. Alternatively, the acid can be activated by conversion to the acid chloride or mixed anhydride and then reacted with the amine ABC to give ABCD.

Other reagents can also be utilized in a similar fashion to introduce $Z\text{-}R^2$, including for example, sulfonyl halides, $R^2SO_2X$, or isocyanates of the formula $R^2NCO$.

Introduction of $R^8$:

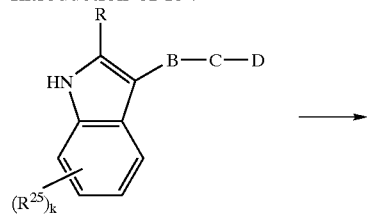

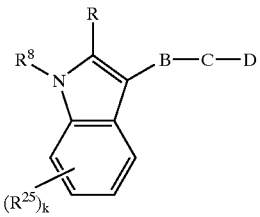

For compounds wherein $R^8$ is attached to the indole nitrogen via an alkyl chain, $R^8$ can be introduced by reacting the indole nitrogen with an alkylating agent $R^8-X$, in which X is a leaving group such as a halogen or mesylate or the like, in a solvent like DMSO, DMF or the like, in the presence of a base to give the final product. For compounds wherein $R^8$ is attached to the indole nitrogen through a $-SO_2-$ group, the indole nitrogen is reacted with a sulfonyl chloride in the presence of a base such as $Et_3N$ in a solvent such as $CH_2Cl_2$ at a temperature of 0°–80° C.

An alternate approach to the synthesis of compounds of formula I comprises the synthesis of the two halves of the molecule (AB and CD), followed by coupling of the two pieces i.e.:

A+B→AB

C+D→CD

AB+CD→ABCD

The synthesis of the AB fragment is the same as previously described. The CD fragment is synthesized as shown below.

C + D → CD

Step 1

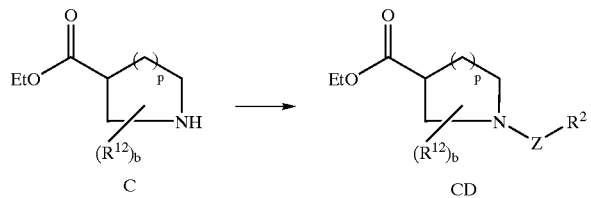

For $Z\text{-}R^2 = -(CH_2)_{1-6} - R^2$, C can be reacted with an aldehyde of the formula $R^2(CH_2)_{1-5}CHO$ in the presence of a reducing agent such as $NaBH_4$, $NaBH(OAc)_3$ or the like in a suitable solvent such as methanol, ethanol, dichloromethane or the like to give CD. Alternatively, C can be reacted with an alkylating agent $R^2-(CH_2)_{1-6}-X$, in which X is a leaving group such as a halogen, mesylate or the like, in a solvent such as DMSO, DMF or the like, in the presence of a base to give CD.

For $Z\text{-}R^2 = C(O) - R^2$, C can be coupled with an acid $R^2CO_2H$ in the presence of a coupling agent such as EDC, DCC or PyBOP. Alternatively, the acid can be activated by conversion to the acid chloride or mixed anhydride and then reacted with the amine C to give CD.

Other reagents can also be utilized in a similar fashion to introduce $Z\text{-}R^2$, including for example, sulfonyl halides, $R^2SO_2X$, or isocyanates of the formula $R^2NCO$.

Step 2

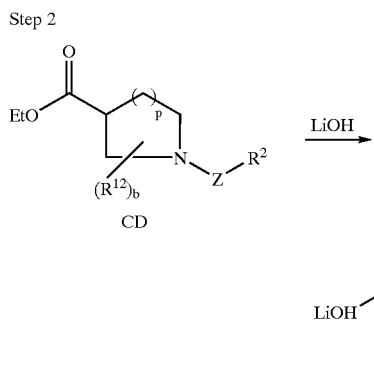

Compound CD is saponified in a mixed solvent such as a combination of EtOH or $CH_3OH$ and water, or a combination of THF, water, and $CH_3OH$, using an alkali metal base such as LiOH or NaOH at a temperature of from 20 to 100° C. to give CD'.

AB + CD' → ABCD

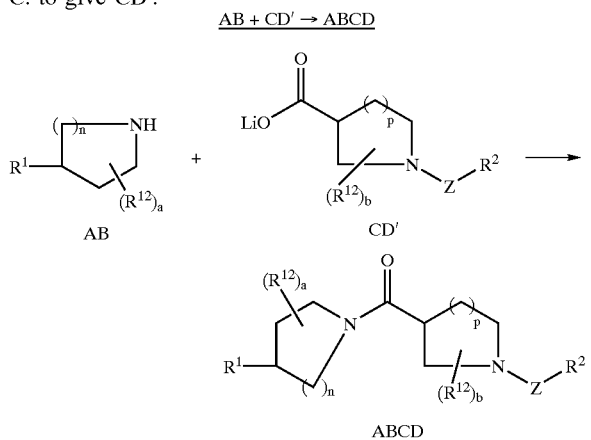

Amine AB can be coupled to CD' using a number of methods well known in the art, such as by using EDC, DCC or PyBOP. Alternatively, CD' can be activated by conversion to the acid chloride or mixed anhydride and then reacted with the amine AB to give ABCD.

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Compounds of formula I can be prepared by the general methods outlined above. Specifically exemplified compounds were prepared as described in the examples below, from starting materials known in the art or prepared as described below. These examples are being provided to further illustrate the present invention. They are for illustrative purposes only; the scope of the invention is not to be considered limited in any way thereby.

Unless otherwise stated, the following abbreviations have the stated meanings in the Examples below:
Me=methyl; Et=ethyl; Bu=butyl; Pr=propyl; Ph=phenyl; t-BOC=tert-butoxycarbonyl;
and Ac=acetyl
DCC=dicyclohexylcarbodiimide
DMAP=4-dimethylaminopyridine
DMF=dimethylformamide
EDCI=1-(3-dimethylaminopropyl)-3-ethylcarbodiimide
HOBT=1-hydroxybenzotriazole
$NaBH(OAc)_3$=sodium triacetoxyborohydride
RT=room temperature
TFA=trifluoroacetic acid
THF=tetrahydrofuran
TEMPO=2,2,6,6-tetramethyl-1-piperidinyloxy, free radical
TLC=thin layer chromatography
HRMS=High Resolution Mass Spectrometry
LRMS=Low Resolution Mass Spectrometry
nM=nanomolar
Ki=Dissociation Constant for substrate/receptor complex
pA2=$-logEC_{50}$, as defined by J. Hey, Eur. J. Pharmacol., (1995), Vol. 294, 329–335.
Ci/mmol=Curie/mmol (a measure of specific activity)

Preparation 1

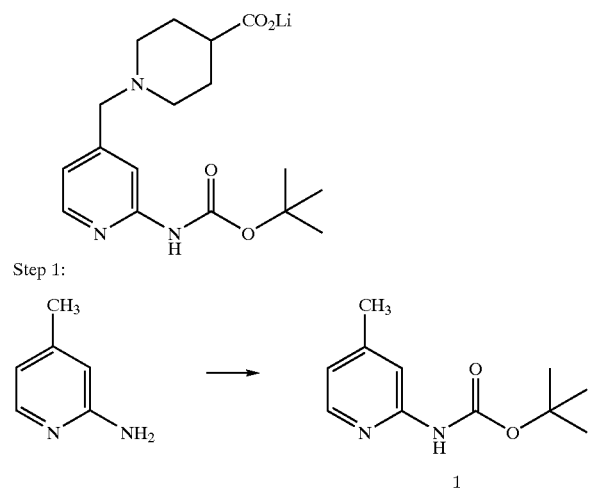

Step 1:

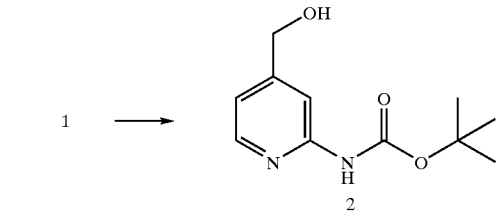

To a solution of 2-amino-4-methylpyridine (10.81 g, 100 mmol) in tert-butanol (250 ml) was added BOC anhydride (26.19 g, 120 mmol). The reaction mixture was stirred at RT overnight, concentrated—dry loaded on silica gel and flash chromatographed (from 30% hexanes/$CH_2Cl_2$ to 0–2% acetone/$CH_2Cl_2$) to produce 1 (15.25 g, 73.32 mmol; 73%) as a white solid.

Step 2:

To a −78° C. solution of 1 (35.96 g, 173 mmol) in THF (1.4 l) was added n-BuLi (272 ml of a 1.4 M solution in hexanes, 381 mmol) in portions over 30 min. The reaction mixture was then allowed to warm up and was stirred for 2 h at RT, resulting in the formation of an orange precipitate. The mixture was cooled back to −78° C., and pre-dried oxygen (passed through a Drierite column) was bubbled through the suspension for 6 h while the temperature was maintained at −78° C. Reaction mixture color changed to yellow during this time. The reaction was then quenched at −78° C. with $(CH_3)_2S$ (51.4 ml, 700 mmol), followed by AcOH (22 ml, 384 mmol). The reaction mixture was allowed to warm up and was stirred for 48 h at RT. Dilution with water and extraction with EtOAc were followed by concentration and flash chromatography (0–15% acetone/CH₂Cl₂) to provide alcohol 2 (20.15 g, 90 mmol; 52%) as a pale yellow solid.

Step 3:

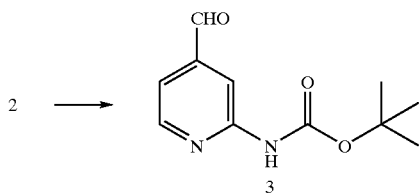

To a solution of alcohol 2 (19.15 g, 85.5 mmol) in CH₂Cl₂ (640 ml) was added a saturated aqueous solution of NaHCO₃ (8.62 g, 103 mmol) and NaBr (444 mg, 4.3 mmol). The reaction mixture was cooled to 0° C., and TEMPO (140 mg, 0.90 mmol) was introduced. Upon vigorous stirring, commercial bleach solution (122 ml of 0.7 M, 85.4 mmol; 5.25% in NaOCl) was added in portions over 40 min. After an additional 20 min at 0° C., the reaction mixture was quenched with saturated aqueous Na₂S₂O₃ and allowed to warm to RT. Dilution with water and extraction with CH₂Cl₂ were followed by concentration and flash chromatography (from 30% hexanes/CH₂Cl₂ to 0–2% acetone/CH₂Cl₂) to afford aldehyde 3 (15.97 g, 71.9 mmol; 84%) as an off-white solid.

Step 4:

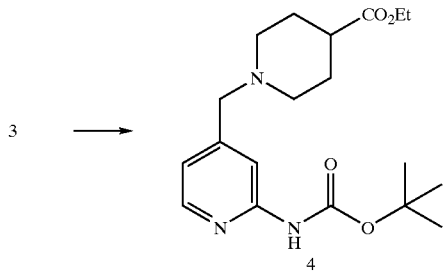

To a solution of aldehyde 3 (11.87 g, 53.5 mmol) in CH₂Cl₂ (370 ml) was added ethyl isonipecotate (9.07 ml, 58.8 mmol) followed by 4 drops of AcOH. The reaction mixture was then stirred for 40 min at RT, after which NaBH(OAc)₃ (22.68 g, 107 mmol) was introduced. The reaction mixture was stirred overnight at RT, neutralized with saturated aqueous NaHCO₃, diluted with water and extracted with CH₂Cl₂. Concentration and flash chromatography (0–4% sat. NH₃ in CH₃OH/CH₂Cl₂) provided 4 (19.09 mg, 52.6 mmol; 98%) as an off-white solid.

Step 5:

To a solution of ester 4 (1.57 g, 4.33 mmol) in a 3:1:1 mixture of THF:water:CH₃OH (10 ml) was added LiOH (0.125 g, 5.21 mmol). The reaction mixture was stirred overnight at RT, concentrated and exposed to high vacuum to obtain crude acid Preparation 1 (1.59 g) as a yellowish solid which was used without purification.

Preparation 2

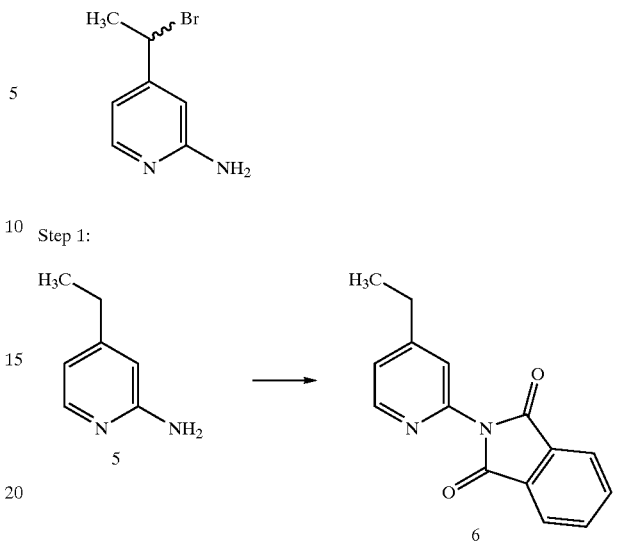

Step 1:

To a solution of 5 (10 g, 79.4 mmol) and DMAP (0.029 g, 0.24 mmol) in CH₂Cl₂ (150 ml) at 0° C. was added phthaloyl dichloride (16.1 g, 79.4 mmol) dropwise. The reaction mixture was stirred at RT overnight, then washed with saturated aqueous NaHCO₃, water, dried and concentrated to give compound 6 as a yellow solid (20 g, 99.8%) which was used without further purification.

Step 2:

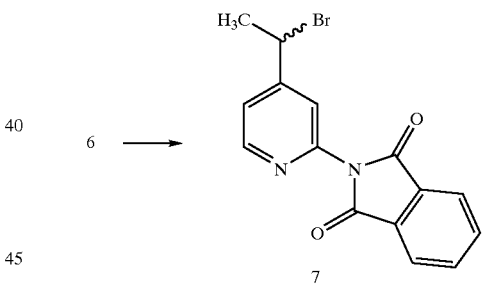

A solution of compound 6, NBS and benzoyl peroxide in CCl₄ was refluxed at 80° C. for 5 h, cooled and stirred at RT overnight. The reaction was filtered and concentrated, and the residue was purified by flash column (30% EtOAc/Hexane) to obtain the desired compound 7.

Step 3:

Compound 7 (0.5 g, 1.5 mmol) and hydrazine (0.5 M in ethanol, 5 ml, 2.5 mmol) were combined and stirred at RT overnight. The reaction was diluted with water and extracted with CH₂Cl₂. The organic layer was dried, concentrated and the residue purified on a flash column (3% CH₃OH in EtOAc) to give the title compound (0.2 g, 66%).

Preparation 3, 3A and 3B

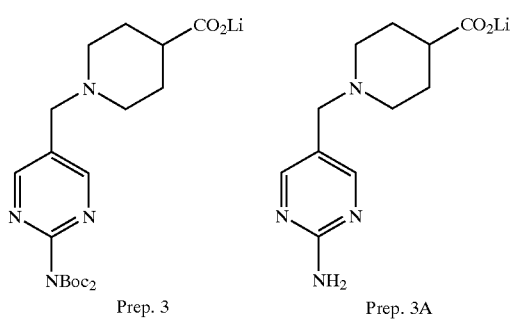
Prep. 3

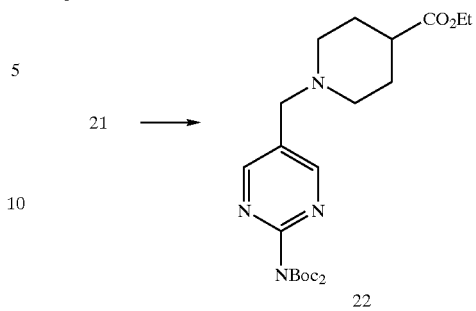
Prep. 3A

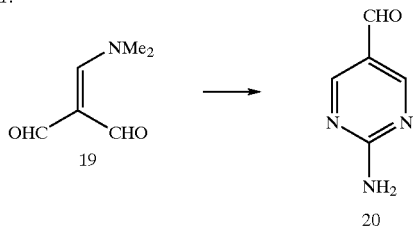
Prep. 3B

Step 1:

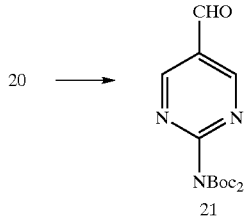
19

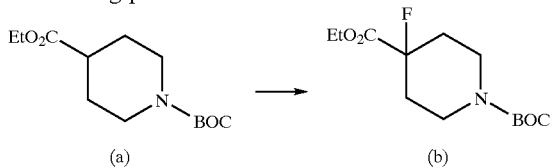
20

To a mixture of dialdehyde 19 (900 mg, 7.1 mmol) and guanidine hydrochloride (678 mg, 7.1 mmol) in absolute EtOH (20 ml) was added sodium ethoxide (483 mg, 7.1 mmol). The reaction mixture was heated at 90° C. for 12 h, cooled to RT, concentrated-dry loaded on silica gel and flash chromatographed (0–10% $CH_3OH$/20–30% acetone/$CH_2Cl_2$) to produce 20 (355 mg, 2.9 mmol; 41%) as a yellowish solid. Alternatively, 20 can be prepared according to the procedure described in JP Patent 63227573.

Step 2:

20 → 21

To a mixture of 20 (166 mg, 1.35 mmol), DMAP (17 mg, 0.14 mmol) and $Et_3N$ (418 µl, 3.00 mmol) in THF (10 ml) was added $(BOC)_2O$ (589 mg, 2.7 mmol). The mixture was stirred at RT for 5 h, concentrated-dry loaded on silica gel and flash chromatographed (1–3% acetone/$CH_2Cl_2$) to produce 21 (117 mg, 0.36 mmol; 27%) as a clear oil.

Step 3:

21 → 22

To a solution of aldehyde 21 (117 mg, 0.36 mmol) in $CH_2Cl_2$ (7 ml) was added ethyl isonipecotate (67 µl, 0.43 mmol) and AcOH (5 µl). 30 min. later, $NaBH(OAc)_3$ (153 mg, 0.72 mmol) was introduced. The mixture was stirred overnight at RT, diluted with $CH_2Cl_2$, washed with aqueous $NaHCO_3$, dried and concentrated, and the crude residue was flash chromatographed (0–4% sat. $NH_3$ in $CH_3OH$/$CH_2Cl_2$) to produce 22 (133 mg, 0.29 mmol; 81%) as a white film.

Step 4:

To a solution of 22 in a 3:1:1 mixture of THF:water:$CH_3OH$ (5 ml) was added LiOH (11 mg, 0.44 mmol). The reaction mixture was stirred overnight at RT, concentrated to dryness and exposed to high vacuum to obtain Preparation 3 (134 mg) as a yellowish solid which was used without purification.

Using a similar procedure, but omitting Step 2, Preparation 3A is obtained.

Prep. 3B is prepared by substituting ethyl 4-(4-fluoropiperidine)carboxylate for ethyl isonipecotate. Ethyl 4-(4-fluoropiperidine)carboxylate is prepared according to the following procedure:

(a) → (b)

A solution of (a) (100 g, 0.389 mol) in THF (400 ml) was added dropwise over 1.0 h to a solution of LDA (233 ml, 2.0 M in THF/heptane/ethyl-benzene, 0.466 mol) in THF (300 ml) at 0° C. The solution was stirred at 0° C. for 30 min, and then transferred by cannula to a 0° C. solution of N-fluorobenzenesulfonimide (153 g, 0.485 mol) in dry THF (600 ml). The reaction mixture was stirred at 0° C. for 30 min, and then at 20° C. for 18 h. The total solvent volume was reduced to approximately one third, and EtOAc (1 l) was added. The solution was washed successively with water, 0.1 N aq. HCl, saturated aq. $NaHCO_3$, and brine. The organic layer was dried over $MgSO_4$, filtered, and concentrated under reduced pressure to yield a crude liquid. Separation by flash chromatography (6:1 hexanes-EtOAc) gave compound (b) (93.5 g, 87%). The BOC protecting group was removed using standard procedures known in the art.

Preparation 4, 4A, 4B, 4C, 4D, 4E

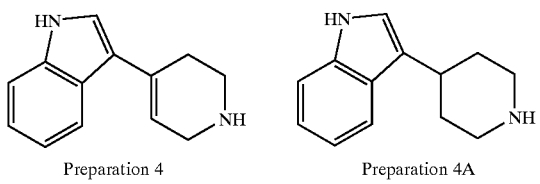

Preparation 4       Preparation 4A

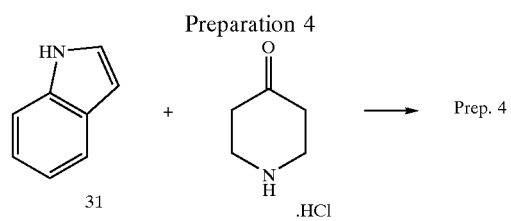

Preparation 4

A solution of indole 31 (10 g) and piperidone hydrochloride (19.7 g) in glacial AcOH (100 ml) and $H_3PO_4$ (40 ml of 1 M solution in water) was heated to 80° C. and stirred for 90 min. The reaction mixture was then poured into ice-cooled $NH_4OH$ (500 ml) and extracted thrice with EtOAc (200 ml) and twice with $CH_2Cl_2$ (200 ml). The organic extracts were combined and concentrated on the rotary evaporator to provide crude Preparation 4. Flash chromatography on silica gel, using 10–20% $NH_3$ saturated $CH_3OH$ in $CH_2Cl_2$ as the eluant, provided pure Preparation 4.

Preparation 4A:

A solution of Preparation 4 (1.1 g) in $CH_3OH$ (100 ml) was treated with 10% Pd/C (250 mg) and ammonium formate (2.8 g) and refluxed overnight. The reaction mixture was filtered through celite. Concentration of the filtrate provided crude Preparation 4A.

In a similar manner, Preparations 4B, 4C, 4D and 4E were prepared:

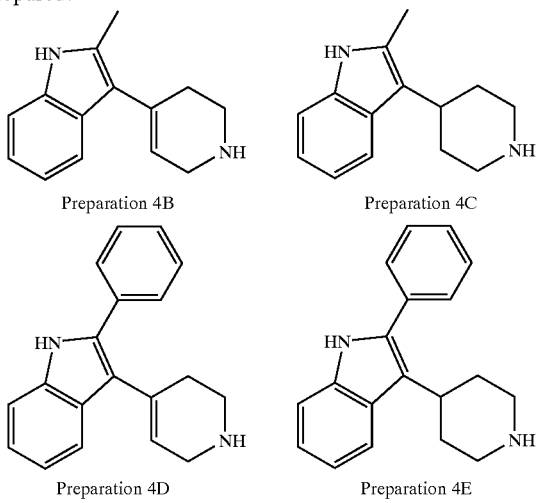

Preparation 4B       Preparation 4C

Preparation 4D       Preparation 4E

Preparation 5

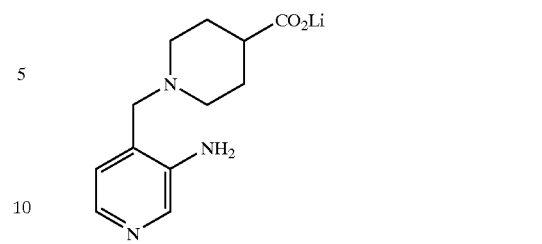

Step 1:

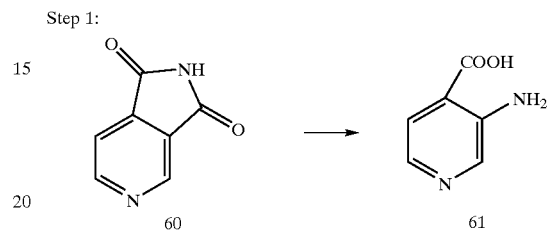

3,4 Pyridine-dicarboximide (10.0 g, 67.5 mmol) was dissolved in 10% aqueous NaOH (162 g) and the solution was cooled to an internal temperature of 7° C. in an ice-salt bath. Bromine (3.6 ml; 70 mmol) was added dropwise. After the addition, the solution was heated for 45 min at a bath temperature of 80–85° C. The yellow solution was then cooled to an internal temperature of 37° C., and glacial AcOH (17 ml) were added dropwise to a pH of 5.5. The resulting mixture was refrigerated overnight. The solid formed was filtered and washed with water (5 ml) and $CH_3OH$ (5 ml). The reaction yielded 6.35 g. of product, m.p. 280–285° C. (decomp.).

Step 2:

$$61 \xrightarrow{\text{LiAlH}_4 / \text{THF}} 62$$

(structure 62: 3-amino-4-hydroxymethylpyridine)

Solid compound 61 (9.5 g, 69 mmol) was carefully added in 3 aliquots to a slurry of $LiAlH_4$ (9.5 g, 250 mmol) in dry THF (200 ml). The resulting hot mixture was stirred at RT for 2 days. After cooling in an ice bath, the reaction was quenched with careful sequential dropwise addition of water (10 ml), followed by 15% aqueous NaOH (10 ml), then by water (30 ml). The resulting solid was filtered through a pad of Celite and washed several times with THF. The oil obtained after evaporation of the solvent solidified on standing. The reaction mixture was purified by flash chromatography on silica gel using 5% $CH_3OH(NH_3)$/EtOAc as eluent, yielding 6.21 g (72%) of 62. LC-MS: m/z=125 (M+1).

Step 3:

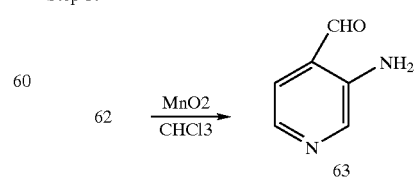

$MnO_2$ (29 g, 334 mmol) was added, in one portion, at RT, to a suspension of 3-amino-4-hydroxymethylpyridine (5.0 g, 40.3 mmol) in CHCl₃ (500 ml) with good stirring. After 2 days, the solid was filtered through a pad of Celite and washed with CHCl₃. Removal of the solvent using reduced pressure yielded 4.2 g (85%) of a yellow solid.

Step 4:

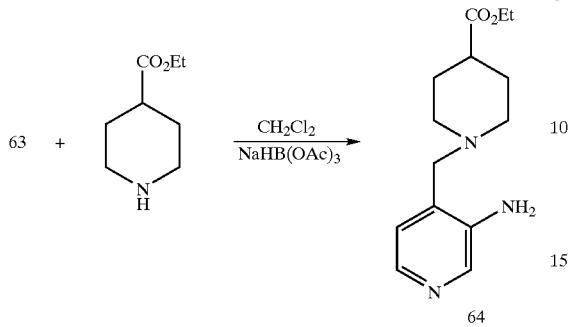

A dry solution of ethyl isonipecotate (12.5 g, 79.5 mmol) and the product of Step 3 (3.33 g, 27.3 mmol) in CH₂Cl₂ (400 ml) was stirred at RT for 1 h, then 60 g of activated 3A molecular sieves were added. The mixture was stirred for an additional 90 min, then NaHB(OAc)₃ (20 g, 96.4 mmol) was added at RT in one portion. After stirring for 3 days, the solid was filtered through a pad of Celite and washed with CH₂Cl₂. The solution was stirred for 15 min with saturated aqueous NaHCO₃ (100 ml), then separated from the aqueous layer. The organic layer was washed 2 more times with saturated aqueous NaHCO₃, then with brine and dried with anhydrous Na₂SO₄. After evaporation of the solvent, the resulting oil was purified by flash chromatography on silica gel using EtOAc:Hexanes:CH₃OH(NH₃) [50:45:5] as eluent. The procedure yielded 6.8 gr.(94%) of 64. FAB-MS: m/z=264 (M+1).

Step 5:
The product of Step 4 (4.75 g, 18.04 mmol) was stirred for 24 h at RT with LiOH monohydrate (1.51 g, 36 mmol) in CH₃OH (75 ml). Removal of the solvent using reduced pressure yielded the title compound as a white solid.

Preparation 6

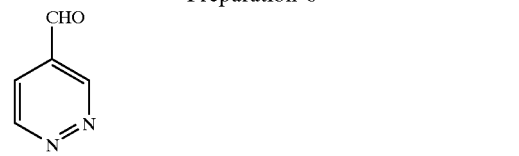

Step 1:

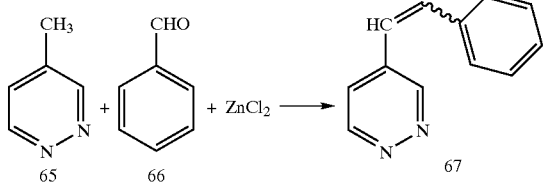

(Modified published procedure: G. Heinisch, E. Luszczak, and M. Pailer: *Monatshefte für Chemie*, 1973 (104), 1372.

65 (4.5 g, 47.8 mmoles), 66 (8.12 g, 76.5 mmoles), and anhydrous ZnCl₂ were heated, under N₂, in a dry apparatus, at a bath temperature of 160° C. for 5 h. The resulting oil was purified by flash chromatography on silica gel using 30% Hexanes/EtOAc, yielding 5.92 grams (67%) of 67.

Step 2:

OsO₄ (5.0 ml in t-butanol, 2.5% w/w) was added to 67 (5.9 g, 32.38 mmoles) dissolved in p-dioxane (87 ml) and water (29 ml). NalO₄ (14.1 g, 65.92 mmoles) was added, with good stirring, in small portions, over a period of 6 h. The mixture was then diluted with p-dioxane and filtered. After removing most of the solvent under reduced pressure, the residue was taken in CH₂Cl₂ (600 ml) and dried over anhydrous Na₂SO₄. After removal of the solvent, the mixture was purified by flash chromatography on silica gel using 5% CH₃OH/CH₂Cl₂ as eluent to obtain Preparation 6. Yield: 2.89 g (82%).

Preparation 7

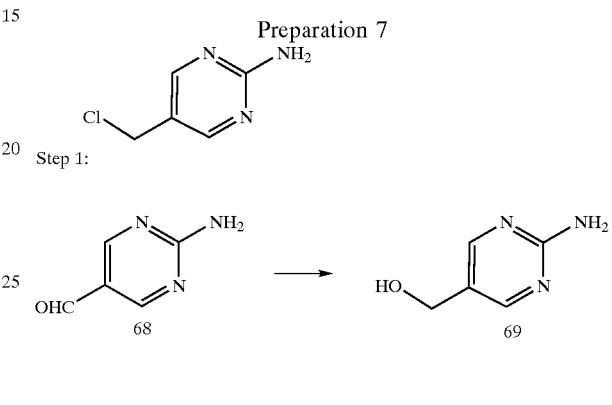

A solution of 68 (50 g, 0.41 mol) in CH₃OH (300 ml) was cooled to 0° C. and carefully treated with NaBH₄ (20 g, 0.53 mol in 6 batches) over 20 min. The reaction was then allowed to warm to 20° C. and was stirred for 4 h. The mixture was again cooled to 0° C., carefully quenched with saturated aqueous NH₄Cl, and concentrated. Flash chromatography (5–10% 7N NH₃—CH₃OH/CH₂Cl₂) provided 69 (31 g, 62%) as a light yellow solid.

Step 2: A slurry of 69 (31 g, 0.25 mol) in CH₂Cl₂ (500 ml) was cooled to 0° C. and slowly treated with SOCl₂ (55 ml, 0.74 mol over 30 min). The reaction was then stirred overnight at 20° C. The material was concentrated, slurried in acetone, and then filtered. The resulting beige solid Preparation 7 was dried overnight in vacuo (38.4 g, 52%, HCl salt).

EXAMPLE 1

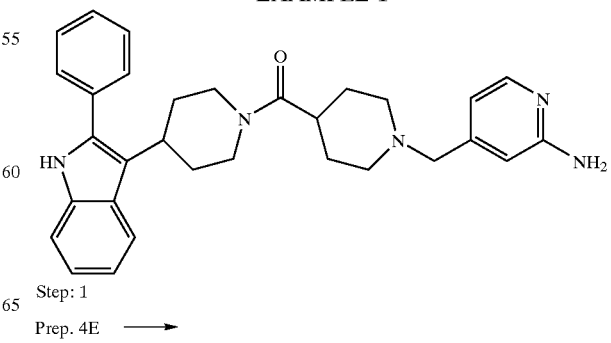

Step: 1
Prep. 4E ⟶

-continued

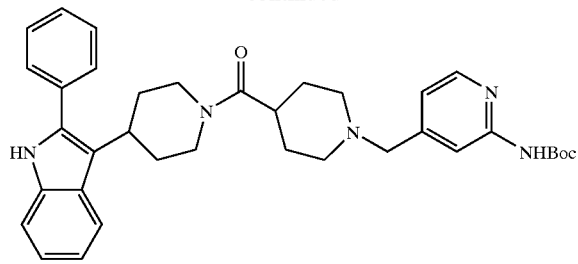

Preparation 1 (1.85 g, 5.43 mmol), Preparation 4E (1.0 g, 3.62 mmol), DEC (1.04 g, 5.43 mmol), HOBT (0.73 g, 5.43 mmol) and DMF/CH$_2$Cl$_2$ (1:1, 30 ml) were combined and stirred at RT overnight. The reaction was diluted with CH$_2$Cl$_2$ and washed with 0.5 N NaOH, water, brine, and dried (Na$_2$SO$_4$). Concentration gave a residue that was triturated with ether to give 11 (2.0 g, 93%). M.S. (M+H)= 594.

Step 2:

Compound 11 (0.18 g, 0.3 mmol) was stirred at RT in a 1:1 mixture of TFA:CH$_2$Cl$_2$ (4 ml) for 2.5 h. The solvent was removed in vacuo and the residue taken up in CH$_2$Cl$_2$ and washed with saturated aqueous NaHCO$_3$. The organic layer was dried (Na$_2$SO$_4$) and concentrated to give a residue that was purified by flash column chromatography (SiO$_2$, 15% CH$_3$OH in EtOAc) to give the title compound (0.14 g, 94%). MS (M+H)=494.

Using a similar procedure and the appropriate starting material of the formula

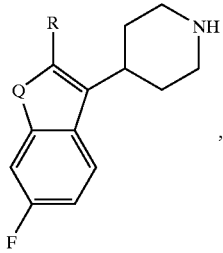

wherein Q is O or S, prepared as described in *J. Heterocyclic Chem.*, 30 (1993), p. 445, compounds of the following structure are prepared:

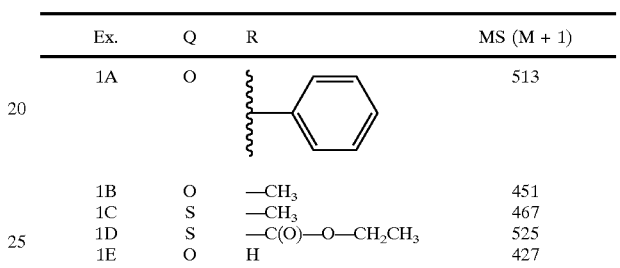

wherein Q and R are as defined in the table

| Ex. | Q | R | MS (M + 1) |
|---|---|---|---|
| 1A | O | ![phenyl] | 513 |
| 1B | O | —CH$_3$ | 451 |
| 1C | S | —CH$_3$ | 467 |
| 1D | S | —C(O)—O—CH$_2$CH$_3$ | 525 |
| 1E | O | H | 427 |

EXAMPLE 2

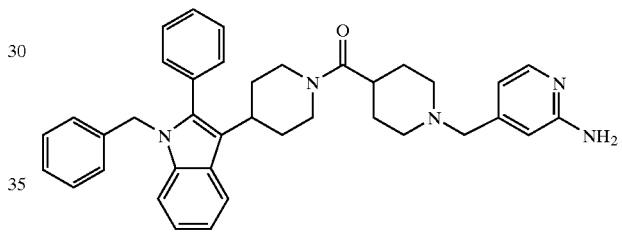

To a solution of Example 1 (0.1 g, 0.2 mmol) in DMF (5 ml) at 0° C. was added NaH (0.016 g, 0.4 mmol). The reaction was stirred at 0° C. for 15 min and at RT for 45 min. Benzyl bromide (0.34 g, 0.2 mmol) was added and the reaction stirred for 2 h. The reaction was diluted with EtOAc and washed with saturated aqueous NH$_4$Cl, water and brine. The organic layer was dried (Na$_2$SO$_4$) and concentrated to give a residue that was purified on a flash column (10% CH$_3$OH in EtOAc) to give the title compound (0.02 g, 17%). MS (M+H)=584.

In a similar manner to the procedure of Example 2, the following compounds were obtained:

| Ex. | Starting Material | Product | Yield | MS (M + H) |
|---|---|---|---|---|
| A |  | | 67% | 602 |

| Ex. | Starting Material | Product | Yield | MS (M + H) |
|---|---|---|---|---|
| B |  | 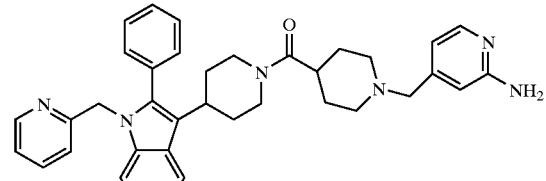 | 72% | 585 |
| C |  | 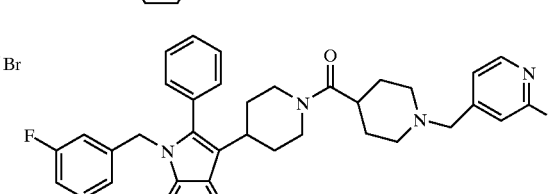 | 15% | 620 |
| D |  | 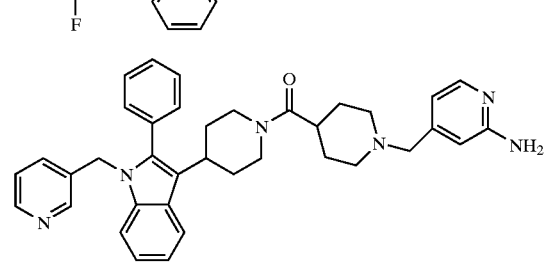 | 61% | 585 |

EXAMPLE 3

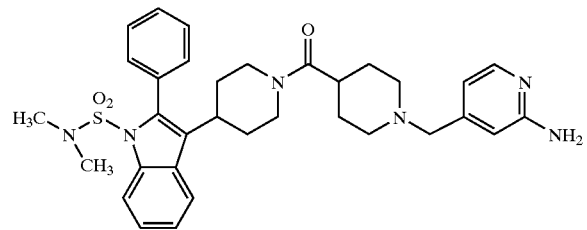

Step 1:
11 →

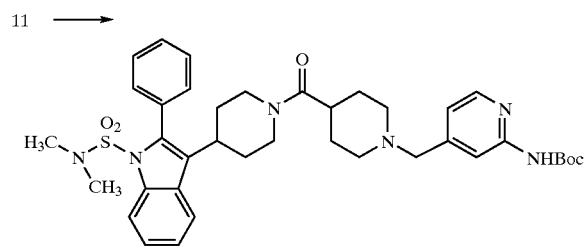

12

A solution of 11 (0.2 g, 0.34 mmol) in CH₂Cl₂/DMF (1:1, 10 ml) at 0° C. was treated with Et₃N (0.1 g) and dimethylsulfamoyl chloride (0.097 g, 0.68 mmol). The reaction was warmed to RT and stirred overnight. Additional dimethylsulfamoyl chloride and Et₃N was added and the reaction heated at 50° C. for 6 h. The reaction was cooled and concentrated, and the residue purified on a flash column (SiO₂, EtOAc to 5% CH₃OH in EtOAc) to give 12 (0.08 g, 34%). MS (M+H)=701.

Step 2:

In a manner similar to that described in Example 1, Step 2, 12 (0.08 g, 0.11 mmol) was converted to the title compound (0.06 g, 100%). MS (M+H)=601.

EXAMPLE 4

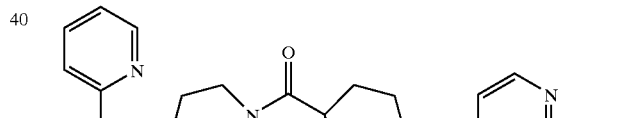

Step 1:

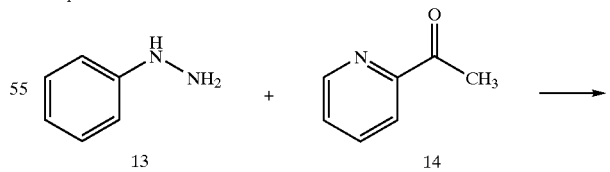

A solution of 13 (5.07 g, 35 mmol of HCl salt which was converted to the free base by treatment with NH₃ saturated CH₃OH) and 14 (4.25 g, 35 mmol) in EtOH (10 mol) was heated to 80° C. for 2 h. The reaction was cooled and the solvent removed in vacuo to give a yellow solid, which was washed with cold EtOH to give 15 (6.9 g, 94%). MS (M+H)=212.

Step 2:

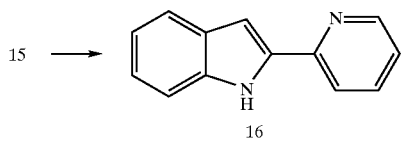

Compound 15 (1.86 g, 8.8 mmol) and polyphosphoric acid (30 g) were heated to 110° C. for 6 h. The reaction was cooled to RT and stirred overnight. The reaction was cooled to 0° C., neutralized with 10% aqueous NaOH and extracted with EtOAc. The combined organic extracts were washed with water and brine and dried (Na₂SO₄) and concentrated to give 16 (1.1 g, 64%). MS (M+H)=195.

Step 3:

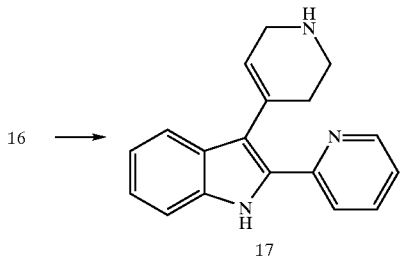

To a solution of 16 (1.6 g, 8.24 mmol) in AcOH (30 ml) at 80° C. was added 4-piperidone hydrochloride (3.7 g, 23.9 mmol) and H₃PO₄ (10 ml). The reaction was stirred at this temperature for 72 h and at 100° C. for 24 h. The reaction was cooled to RT and poured into ice/NH₄OH and extracted with EtOAc. The combined organic layers were washed with water and brine, dried (Na₂SO₄) and concentrated. The residue was purified on a flash column (20% EtOAc in hexane to 10% CH₃OH/NH₃ in CH₂Cl₂) to give 17 (0.5 g, 44% based on recovered starting material). MS (M+H)=276.

Step 4:

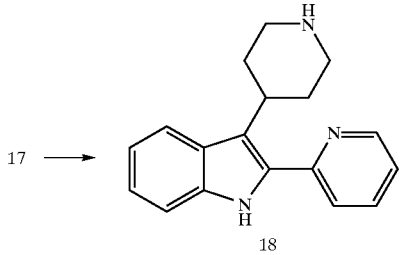

Compound 17 (0.5 g, 1.8 mmol), 10% Pd/C (0.05 g), and NH₄CHO₂ (0.92 g, 14.5 mmol) were combined in CH₃OH (20 ml) and heated to reflux overnight. The reaction was cooled, filtered through celite, and the filter cake washed with additional CH₃OH. The solvent was concentrated to give 18 (0.6 g, >100%) which was used without further purification. MS (M+H)=278.

Step 5:

In a manner similar to that described in Example 1, steps 1 and 2, 18 (0.6 g, 2.2 mmol) was converted to the title compound (0.08 g, 72% over two steps). MS (M+H)=495.

EXAMPLE 5

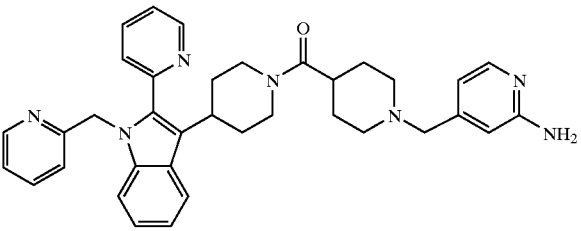

In a manner similar to that described in Example 2, the compound of Example 4 (0.12 g, 0.24 mmol) was converted to the title compound (0.05 g, 36%). MS spectrum (M+H)=586.

EXAMPLE 6

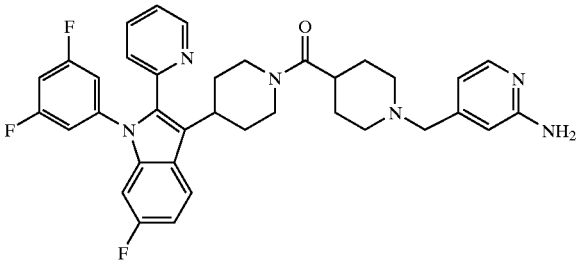

Step 1:

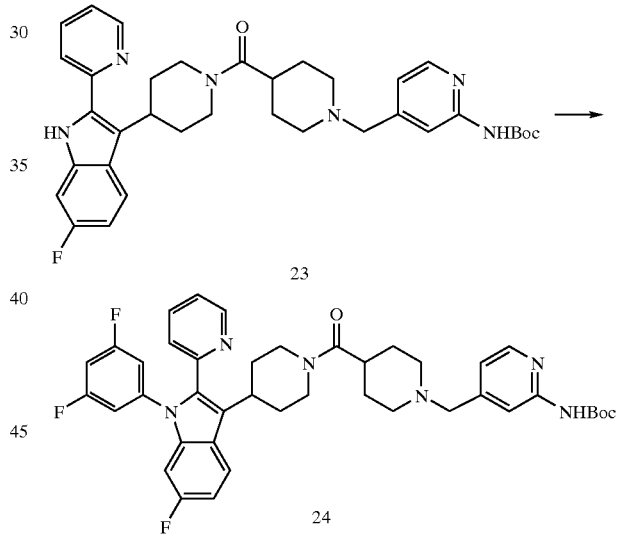

Compound 23 (0.08 g, 0.13 mmol), 3,5-difluorophenylboronic acid (0.04 g, 0.26 mmol), Cu(OAc)₂ (0.005 g, 0.026 mmol), TEMPO (0.023 g, 0.143 mmol), pyridine (0.021 g, 0.26 mmol) and 3 Å molecular sieves (0.1 g) were combined in CH₂Cl₂ (10 ml) and heated to reflux overnight. The CH₂Cl₂ was removed in vacuo, DMF (5 ml) was added and the reaction heated to 70° C. for 7 h. The reaction was cooled to RT and stirred for 48 h. The solvent was removed and the residue purified using flash chromatography (SiO₂, 3% CH₃OH in EtOAc) to give 24 (0.031 g, 33%). MS (M+H)=725.

Step 2:

In a manner similar to that described in Example 1, Step 4, 24 (0.031 g) was converted to the title compound (0.02 g). MS (M+H)=625.

Using the appropriate starting material and the procedures of Examples 4 and 5, the following compounds were prepared:

| Ex. | Product | MS (M + H) |
|---|---|---|
| 6A | | 605 |
| 6B | | 513 |
| 6C | | 604 |
| 6D | | 623 |
| 6E | | 606 |
| 6F | | 608 |

-continued

| Ex. | Product | MS (M + H) |
|---|---|---|
| 6G | | 587 |
| 6H | | 620 |
| 6I | | 619 |
| 6J | | 479 |
| 6K | | 622 |
| 6L | | 509 |

-continued
| Ex. | Product | MS (M + H) |
|---|---|---|
| 6M | 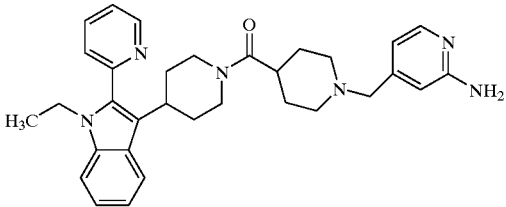 | 551 |
| 6N | 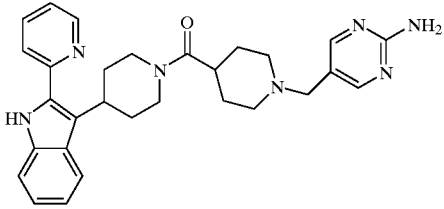 | 496 |
| 6O | 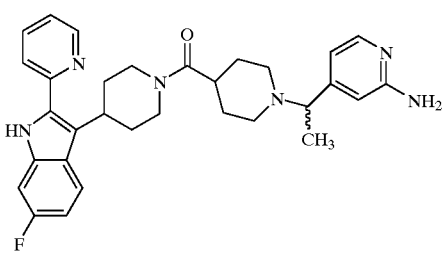 | 527 |
| 6P | 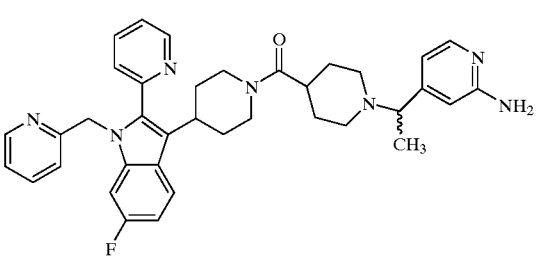 | 618 |
| 6Q | 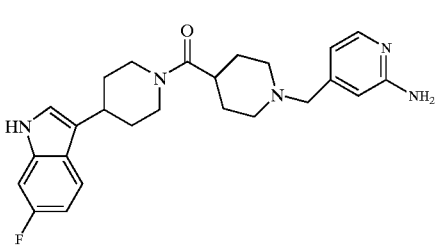 | 436 |
| 6R | 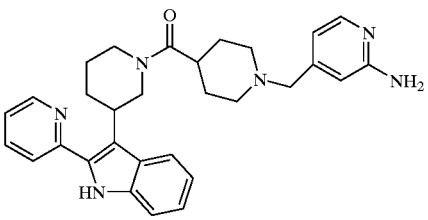 | 495 |

EXAMPLE 7 AND 7A

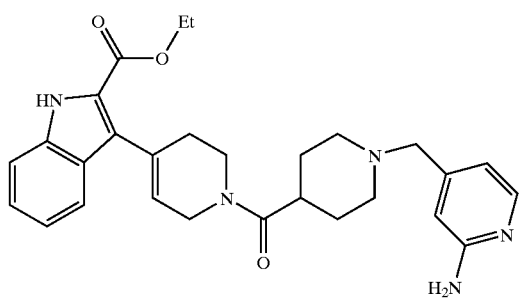

Step 1:

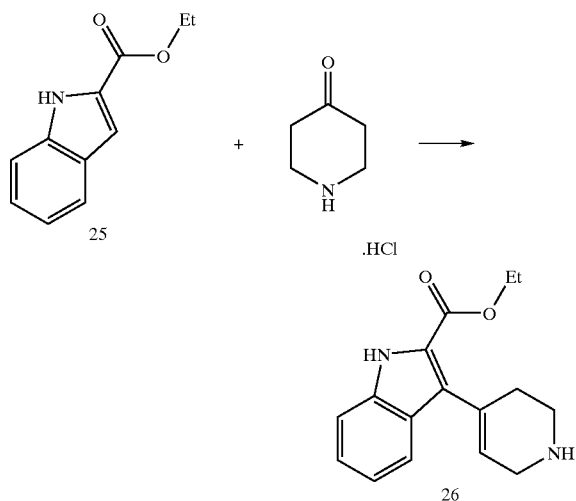

A mixture of 25 (10 g, 51.2 mmol) and the piperidone HCl salt (8 g, 51.2 mmol) in AcOH (100 ml) and H$_3$PO$_4$ (40 ml of 1 M solution in water) was refluxed for 2 days. The reaction mixture was then concentrated in vacuo, partitioned between EtOAc (200 ml) and water (100 ml) and basified with KOH. The organic layer was isolated, washed with brine and dried with anhydrous Na$_2$SO$_4$. Concentration in vacuo provided crude 26 which was purified by flash chromatography on a silica gel column, eluting with 5% CH$_3$OH in CH$_2$Cl$_2$ (with 0.5% saturated aqueous NH$_4$OH). Pure 26 was obtained (2.5 g, 18% yield) as a light brown solid.

Step 2:

26 + Preparation 1 $\xrightarrow[\text{DMF}]{\text{EDC} \atop \text{HOBT}}$

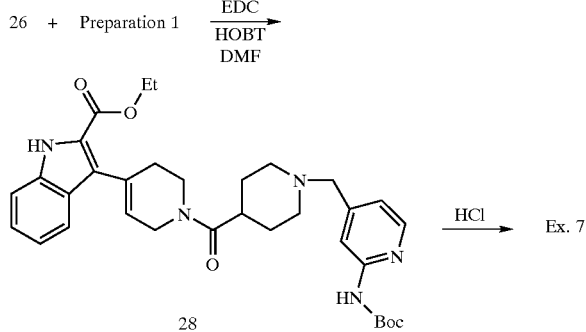

$\xrightarrow{\text{HCl}}$ Ex. 7

26 (1.15 g) was coupled with Preparation 1 with EDC under standard amide-coupling conditions. After work up, flash chromatography over silica gel using 5% CH$_3$OH in CH$_2$Cl$_2$ with 0.5% saturated aqueous NH$_4$OH as eluant provided pure 28 (1.5 g, 60% yield). HCl deprotection of the pyridine amine provided, quantitatively, the title compound. MS (ES) m/e=488 (MH$^+$).

Starting from Preparation 4B, the following compound was made in a similar manner to Example 7:

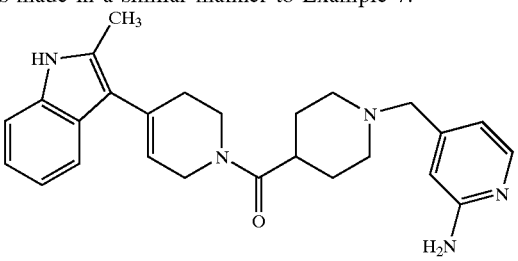

Ex. 7B: MS(ES) m/e = 430 (MH$^+$).

EXAMPLE 8

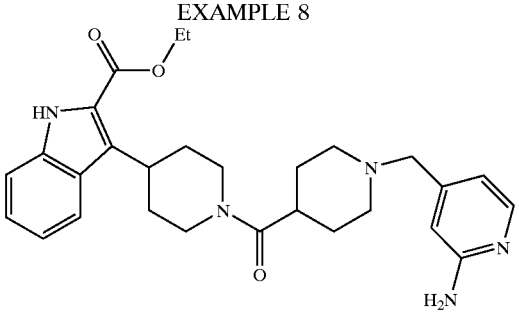

Step 1:

26 $\xrightarrow{\text{H}_2 \atop \text{Pd(OH)}_2}$ 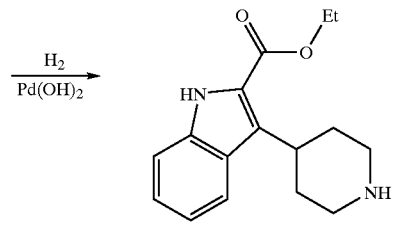

26 (1.4 g) was dissolved in EtOH, treated with Pd(OH)$_2$ (0.1 g), acidified with HCl (12N, 1 ml) and stirred under a hydrogen atmosphere supplied by a balloon for 60 h. The reaction mixture was then filtered through celite and concentrated to provide 29.

Step 2:

29 + Preparation 1 $\xrightarrow[\text{DMF}]{\text{EDC} \atop \text{HOBT}}$

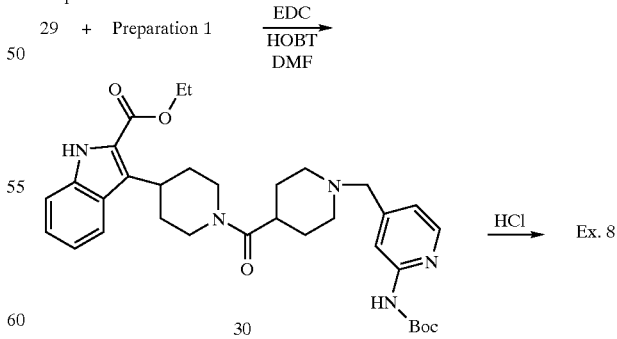

$\xrightarrow{\text{HCl}}$ Ex. 8

29 (0.8 g) was coupled with Preparation 1 under standard amide-coupling conditions to provide 30 (1.1 g, 64% yield), as an off-white solid after flash chromatography over silica gel (5% CH$_3$OH in CH$_2$Cl$_2$ with 0.5% saturated aqueous NH$_4$OH). HCl deprotection of the pyridine amine provided, quantitatively, the title compound as an off-white solid. MS (ES) m/e=490 (MH+).

EXAMPLE 9

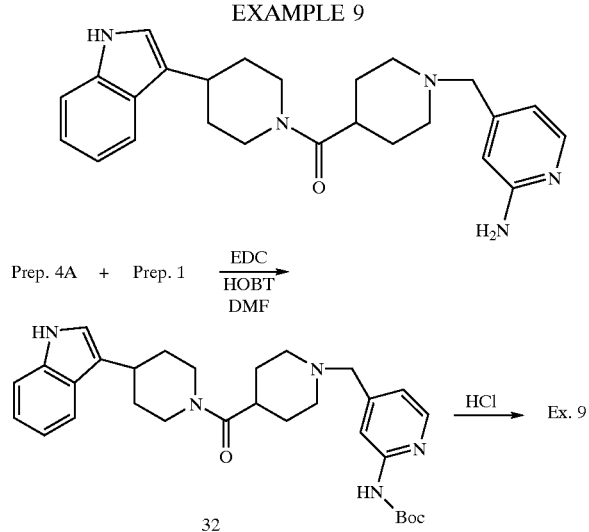

Starting from Preparation 4A, the title compound was made in a manner similar to Example 7. MS (ES) m/e=418 (MH+).

EXAMPLES 10, 10A, 10B AND 10C

A solution of isopropylamine (59 mg, 1 mmol) in toluene (10 ml), at RT was treated with trimethylaluminum (2.0 M solution in toluene, 2 mmol) and stirred at RT for 30 min, whereupon compound 28 (0.21 g, 0.35 mmol) was added. The reaction mixture was heated to 80° C., stirred overnight at that temperature and then cooled to RT and carefully quenched with saturated aqueous $Na_2SO_4$. After the bubbling of hydrogen had ceased, solid $Na_2SO_4$ was added to absorb water. Filtration through a filter paper and concentration in vacuo provided crude Example 10 and 33. The entire product mixture was treated with HCl (1.5 N $CH_3OH$/dioxane) and stirred at 60° C. for 2 h. The mixture was then concentrated in vacuo and run through a silica gel flash column (10% $CH_3OH$ in $CH_2Cl_2$ with 0.5% saturated aqueous $NH_4OH$). Two products were obtained:

Example 10 (45 mg, off-white solid) MS (ES) m/e=586 (MH+); and

Example 10A (7 mg, light-orange solid) MS (ES) m/e=501 (MH+).

In a similar manner, using 28 and commercially available 1-methyl-4-(methylamino)piperidine, Example 10B was prepared:

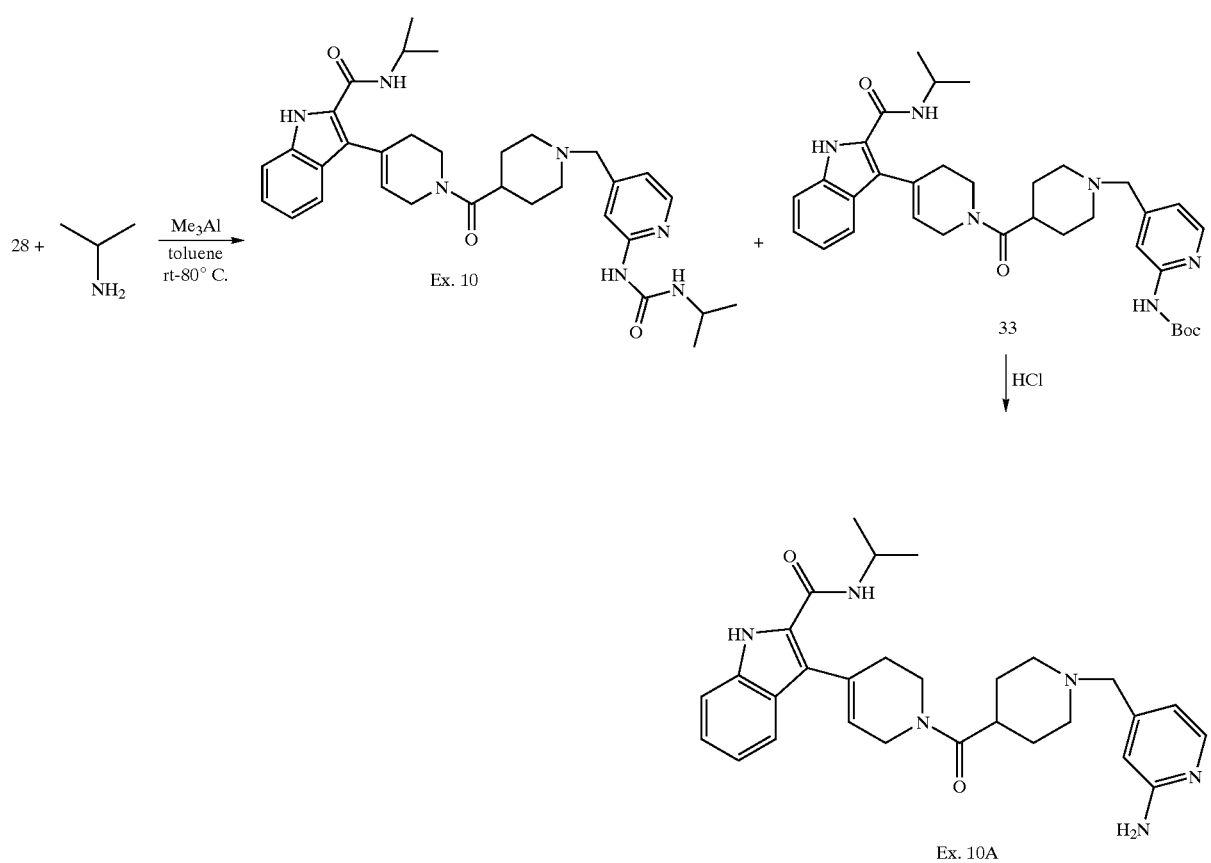

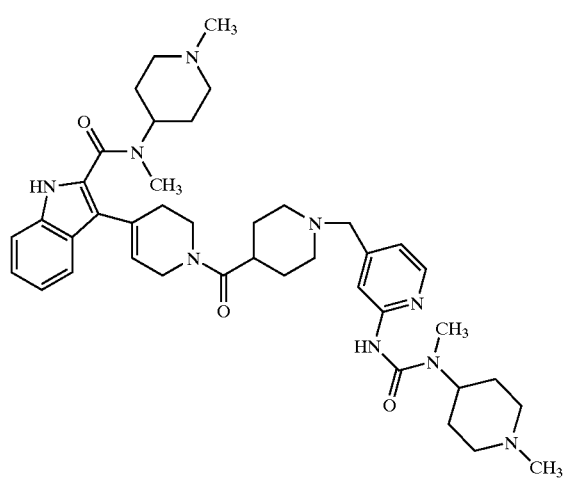
Ex. 10B: MS(ES) m/e = 724 (MH⁺).
In a similar manner, using 28 (only the t-butyl carbamate portion of the molecule, and not the ester, reacted with the amine) and commercially available 2-aminopyridine, Example 10C was prepared:
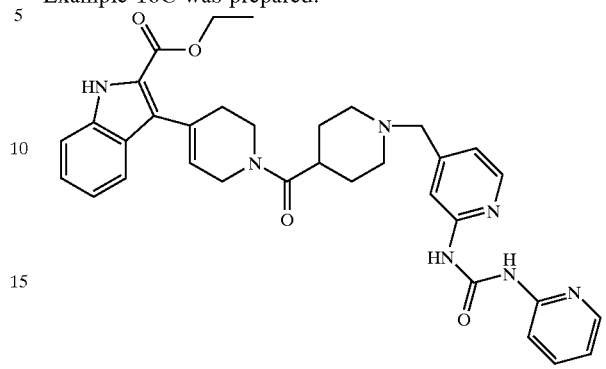
Ex. 10C: MS (ES) m/e = 608 (MH⁺).
EXAMPLES 11 AND 11A
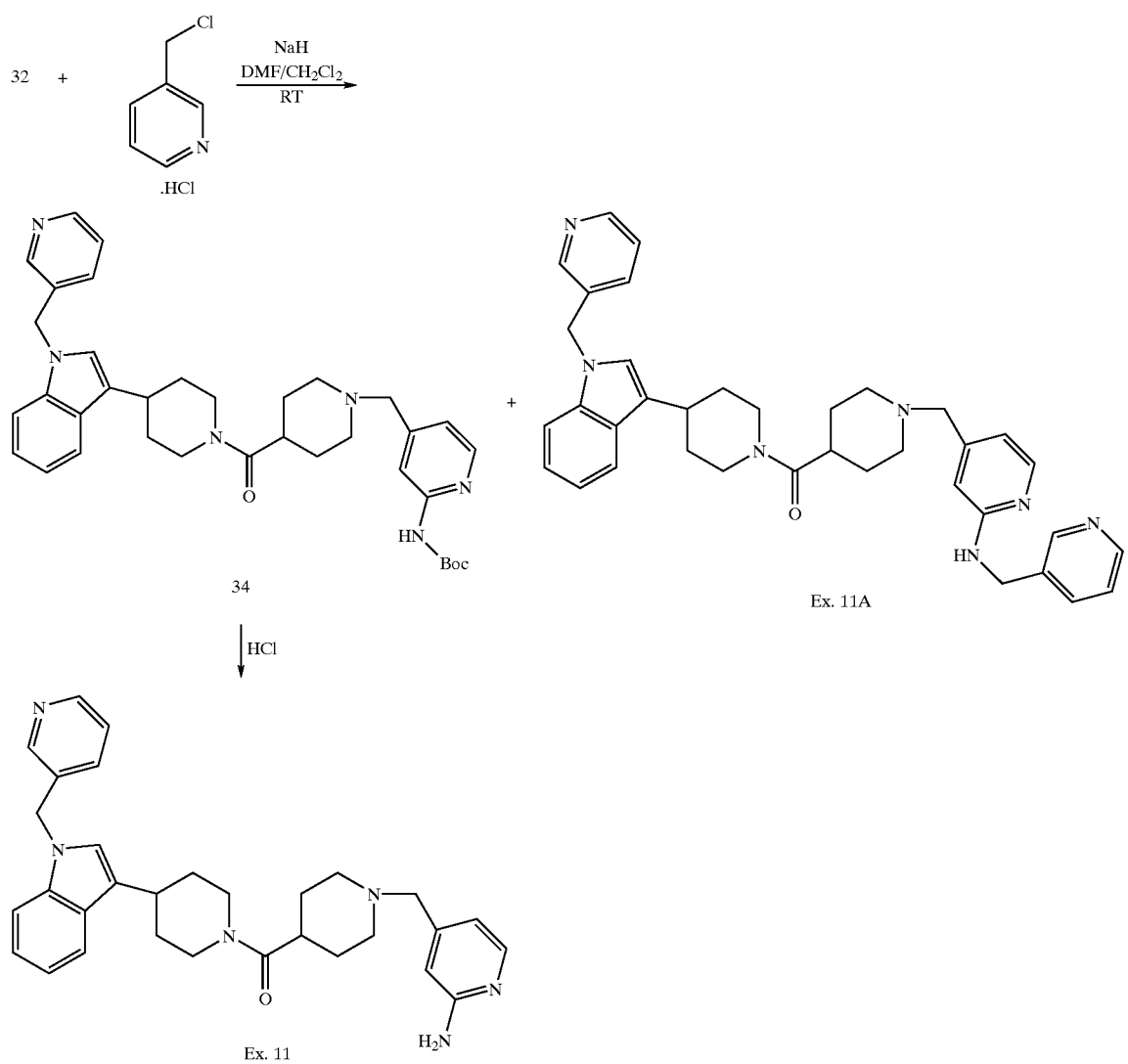

A solution of 32 (0.2 g, 0.38 mmol) in DMF (5 ml) at RT was treated with NaH (0.12 g, 60% dispersion in mineral oil) and stirred for 30 min. 3-Picolyl chloride (0.38 mmol, HCl salt) was then added and the resulting mixture stirred overnight. CH$_2$Cl$_2$ (20 ml) was then added to solubilize the substrate and the mixture stirred over the weekend. The reaction was then quenched with saturated aqueous Na$_2$SO$_4$ until the bubbling of hydrogen ceased and dried with solid Na$_2$SO$_4$, filtered and concentrated in vacuo. The crude product mixture was taken up in 2 N HCl (CH$_3$OH/dioxane), stirred for 2 h at 60° C. and concentrated in vacuo. Silica gel prep plate separation (10% CH$_3$OH in CH$_2$Cl$_2$ with 0.3% saturated aqueous NH$_4$OH) afforded Example 11A (40 mg) as an off-white solid (MS (ES) m/e=509 (MH$^+$)) and Example 11 (22 mg) as an off-white solid (MS (ES) m/e=600 (MH$^+$)).

Using 32 and 2-picolyl chloride in a procedure similar to Example 11, the following compound was prepared:

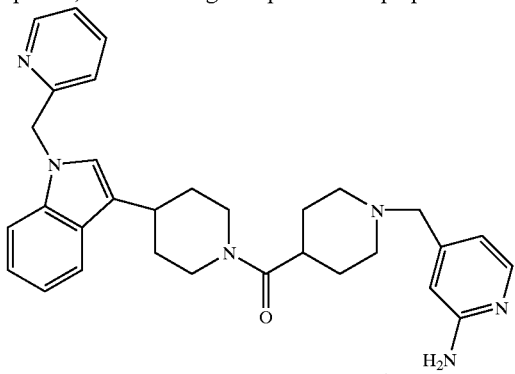

Ex. 11B: MS (ES) m/e = 509 (MH$^+$).

EXAMPLE 12

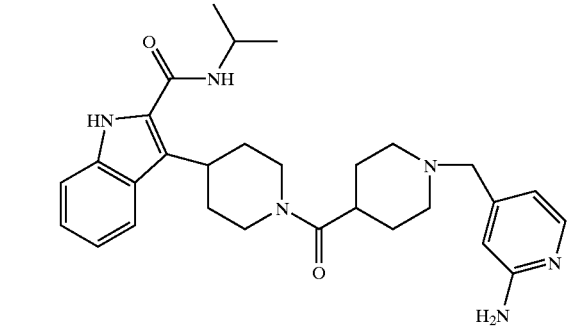

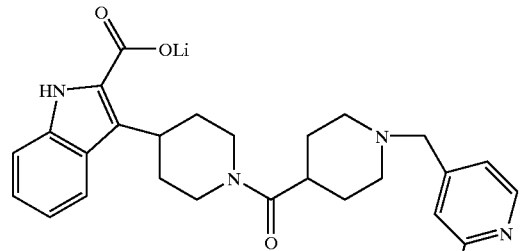

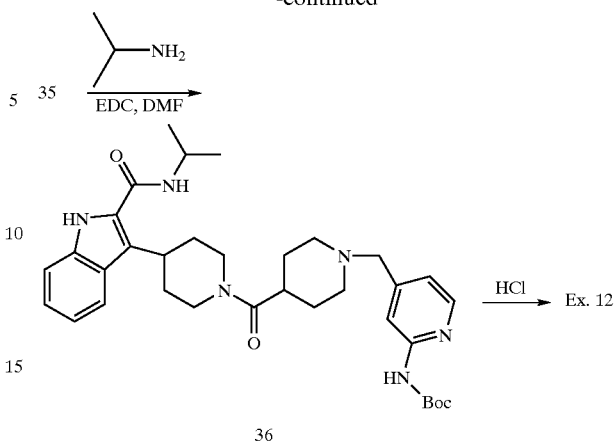

A solution of 30 (1.1 g) in dioxane/H$_2$O (12:1, 25 ml) was treated with LiOH.H$_2$O (0.3 g) and stirred overnight at 70° C. Concentration in vacuo provided crude 35 that was used in the next step without further purification. 35 (0.27 g) was coupled with isopropyl amine, using EDC under standard amide-coupling conditions, to provide crude 36. Separation on a silica gel prep plate (10% CH$_3$OH in CH$_2$Cl$_2$ with 0.25% saturated aqueous NH$_4$OH) provided pure 36. Cleavage of the BOC-protecting group with HCl provided the title compound (90 mg, HCl salt) as an off-white solid. MS (ES) m/e=503 (MH$^+$).

Using the appropriate amine in the procedure of Example 12, the compounds of the following structure were prepared:

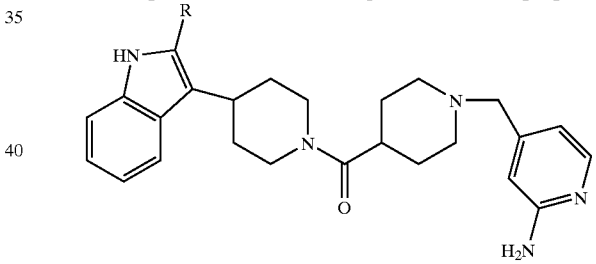

wherein R is as defined in the table

| Ex. | R | Physical Data |
|---|---|---|
| 12A | —C(O)—NH—CH$_3$ | MS (ES) m/e = 475 (MH$^+$) |
| 12B | —C(O)—NH—CH$_2$CH$_3$ | MS (ES) m/e = 489 (MH$^+$) |
| 12C | ![structure] | MS (ES) m/e = 616 (MH$^+$) |
| 12D | ![structure] | MS (ES) m/e = 572 (MH$^+$) |

EXAMPLE 13

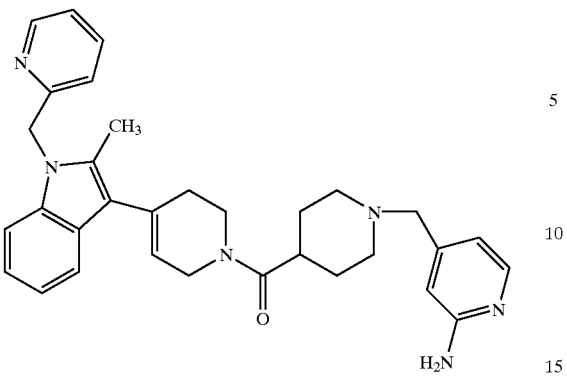

Example 13 was prepared using Preparation 4B and 2-picolyl chloride in a procedure similar to Example 12. MS (ES) m/e=521 (MH+).

Using Preparation 4B or Preparation 4C and the appropriate halide, the following compounds were prepared in a manner similar to Example 13:

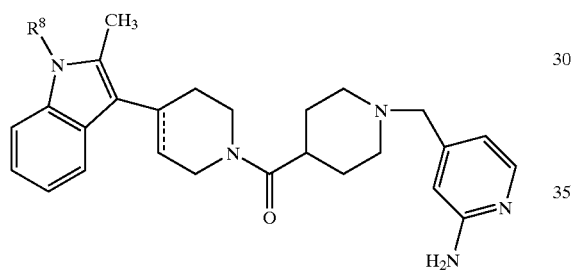

wherein R is as defined in the table

| Ex. | R⁸ | Optional Double Bond | Physical Data |
|---|---|---|---|
| 13A | benzyl | present | MS (ES) m/e = 520 (MH+) |
| 13B | CF₃—(CH₂)₃— | present | MS (ES) m/e = 540 (MH+) |
| 13C | CH₃—CH₂— | present | MS (ES) m/e = 458 (MH+) |
| 13D | (2-pyridyl)methyl | absent | MS (ES) m/e = 523 (MH+) |
| 13E | H | absent | MS (ES) m/e = 432 (MH+) |
| 13F | (3-pyridyl)methyl | absent | MS (ES) m/e = 523 (MH+) |

EXAMPLE 14

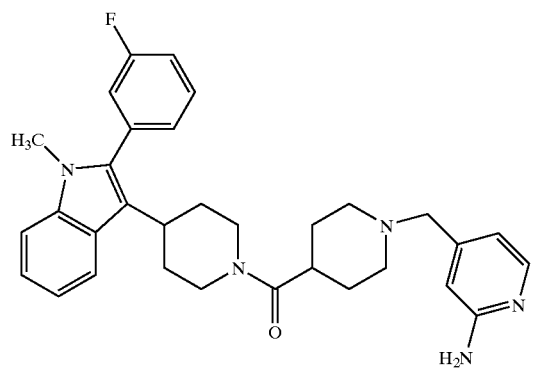

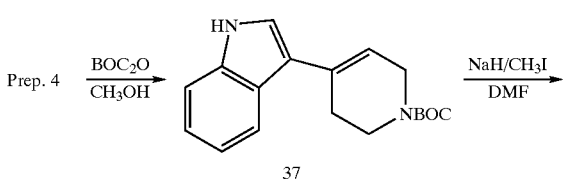

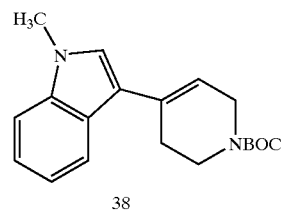

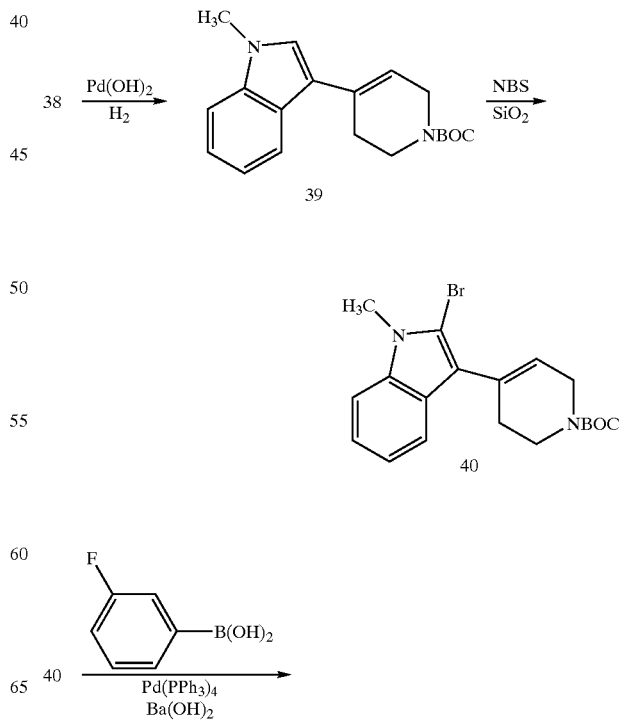

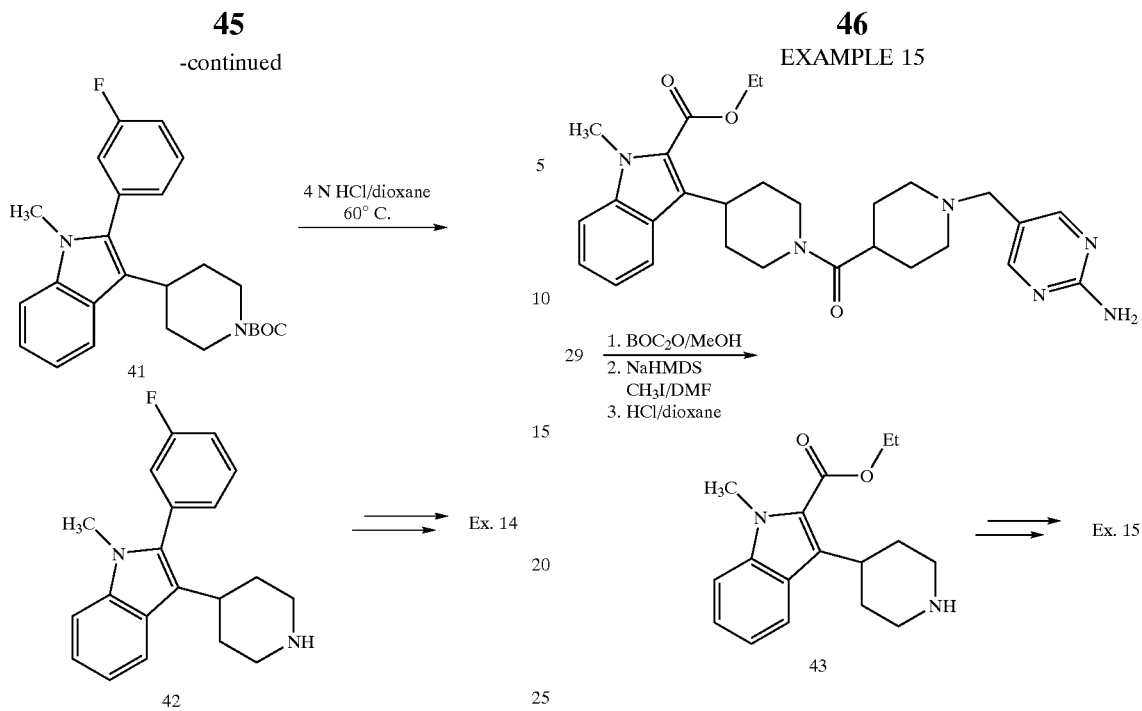

A solution of Preparation 4 (4.5 g, 22.6 mmol) in CH₃OH (100 ml) was treated with BOC₂O (9.9 g, 45.2 mmol) and stirred overnight. Concentration to dryness and purification by flash chromatography on silica gel using 7% NH₃ saturated CH₃OH in CH₂Cl₂ provided clean 37. A solution of 37 (2.5 g, 8.4 mmol) in DMF (15 ml) at 0° C. was treated with 3 mole equivalents of NaH and stirred for ten minutes at 0° C. and 45 min at RT. One mole equivalent of CH₃I was added and the mixture stirred overnight. The mixture was then concentrated and partitioned between NH₄Cl saturated water (100 ml) and EtOAc (100 ml). The organic layer was isolated and concentrated to provide crude 38 (2.3 g), which was converted to 39 in similar manner to 29.

All of 39 was taken up in CH₂Cl₂ (50 ml) and treated successively with silica gel (15 ml), and N-bromosuccinimide (0.3 g, 1.6 mmol) in the dark and stirred at RT for 1.5 h. Filtration through a fritted funnel and concentration provided crude 40 which was purified on a silica gel flash column, eluting with 20% EtOAc in hexane.

A mixture of 40 (0.45 g, 1.14 mmol), 3-fluorophenyl boronic acid (176 mg, 1.26 mmol), Ba(OH)₂·8H₂O (0.54 g, 1.7 mmol) and tetrakis(triphenylphosphine)palladium(0) (26 mg, 0.022 mmol) in dimethoxyethane/H₂O (2:1, 100 ml) was refluxed for 4 h. and then concentrated in vacuo. The crude product mixture was partitioned between CH₂Cl₂ (100 ml) and water (75 ml). The organic layer was isolated and dried with MgSO₄. Separation on silica gel prep plates using hexane/EtOAc (9:1) as eluant provided pure 41 (0.4 g). HCl cleavage of the BOC-protecting group gave amine 42 that was converted to the title compound in a similar manner to Example 7. MS (ES) m/e=526 (MH⁺).

With the piperidine amine protected with a BOC group, the indole nitrogen of 29 was deprotonated with NaHMDS in DMF and alkylated with CH₃I. HCl-deprotection of the resulting intermediate provided 43. Standard amide-coupling of 43 and Preparation 3A gave the title compound. MS (ES) m/e=505 (MH⁺).

EXAMPLE 16

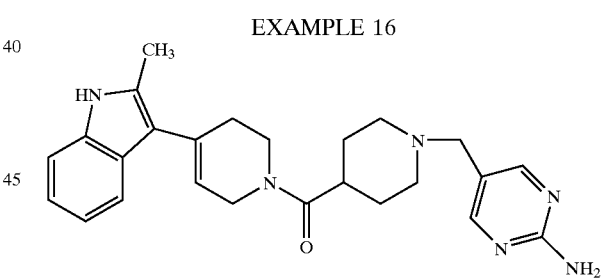

The title compound was obtained by standard amide-coupling of Preparation 4B to Preparation 3. MS (ES) m/e=431 (MH⁺).

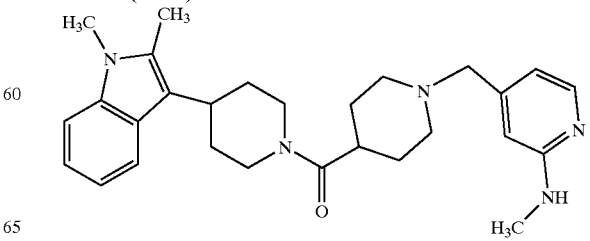

EXAMPLE 17

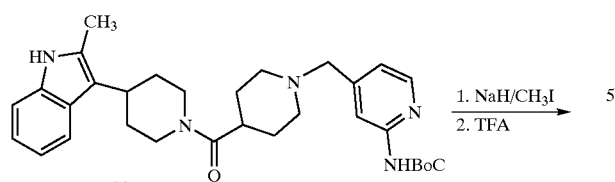

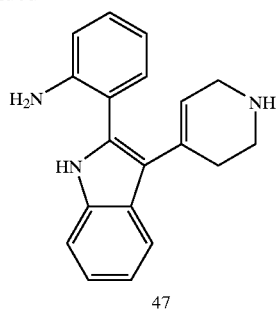

A solution of 44 (225 mg, 0.42 mmol), obtained by amide-coupling of Preparation 4C and 28 in DMF (3 ml) at 0° C. was treated with NaH (51 mg, 1.3 mmol) and stirred at 0° C. for 10 min and at RT for 30 min. $CH_3I$ (0.43 mmol) was then added and the resulting mixture stirred overnight at RT. The reaction mixture was then concentrated in vacuo and partitioned between saturated aqueous $NH_4Cl$ (30 ml) and $CH_2Cl_2$ (50 ml). Concentration and flash chromatography on silica gel (2% $NH_3$ saturated $CH_3OH$ in $CH_2Cl_2$) provided the N,N'-dimethyl amine precursor of the title compound (48 mg). Cleavage of the BOC group with TFA provided the title compound. MS (ES) m/e=460 (MH$^+$).

EXAMPLE 18

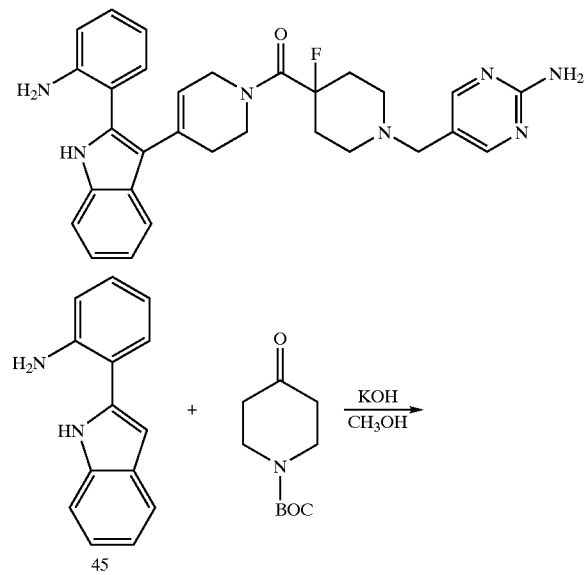

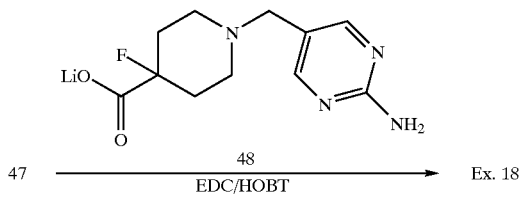

A mixture of 45 (2.1 g, 10 mmol), BOC-piperidone (3.4 g, 17 mmol) and KOH (0.28 g, 5 mmol) in $CH_3OH$ (150 ml) was refluxed for eight days. The reaction mixture was then concentrated in vacuo, partitioned between water (50 ml) and $CH_2Cl_2$ (100 ml), and acidified with AcOH. The organic layer was isolated and concentrated to provide crude 46. Cleavage of the BOC group with HCl provided 47. Standard amide-coupling of 47 to 48 (Prep. 3B) using EDC provided the title compound. MS (ES) m/e=526 (MH+).

EXAMPLE 19

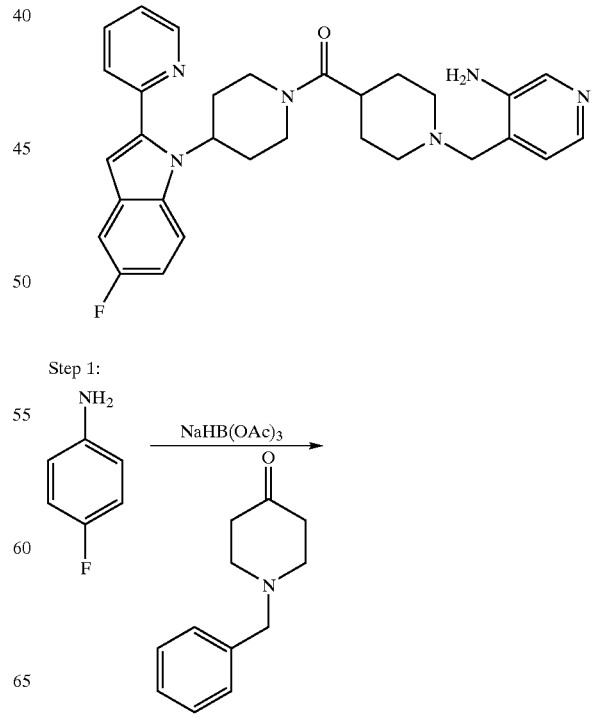

Step 1:

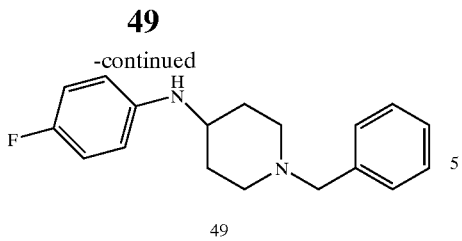

49

4-Fluoro aniline (13.3 g, 120 mmol) and 1-benzyl-4-piperidone (18.9 g, 100 mmol) were stirred at RT, under $N_2$, in dry $CH_2Cl_2$ (120 ml) for 4 h. $NaHB(OAc)_3$ (32 g, 151 mmoles) was then added and the mixture stirred at RT for 60 h. After dilution with $CH_2Cl_2$ (100 ml), the solution was stirred for 30 min. with saturated aqueous $NaHCO_3$. The aqueous layer was separated and extracted with $CH_2Cl_2$. The combined organic solutions were washed with brine and dried over anhydrous $Na_2SO_4$. The reaction mixture was purified by flash chromatography on silica gel using 30% EtOAc/Hexanes as eluent, followed by 50% EtOAc/Hexanes, then by 20% Hexanes/EtOAc. Yield: 22.13 g. (78%). MS: m/z=285 (M+1).

Step 2:

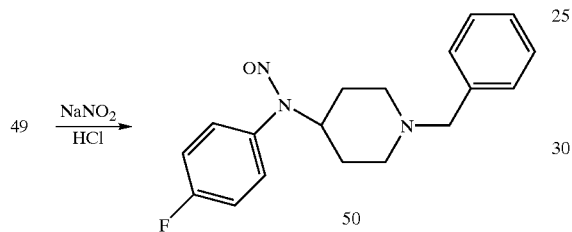

4 M HCl in p-dioxane (20 ml, 80 mmol) was added to a precooled solution (ice bath) of 49 (4.06 g, 14.28 mmol) in $CH_2Cl_2$ (80 ml). To the resulting mixture were added, dropwise with good stirring, $NaNO_2$ (1.97 g, 28.6 mmol) dissolved in water (10 ml). After the addition, the mixture was stirred in the ice bath for another 3 h, then made basic with saturated aqueous $NaHCO_3$ and stirred at RT for an additional 30 min. After separating the organic layer, the aqueous layer was extracted with $CH_2Cl_2$. The organic layers were combined, washed with brine and dried over anhydrous $Na_2SO_4$. The reaction mixture was purified by flash chromatography on silica gel using 20% EtOAc/Hexanes as eluent. Yield: 3.0 g (67%). MS: m/z=314 (M+1).

Step 3:

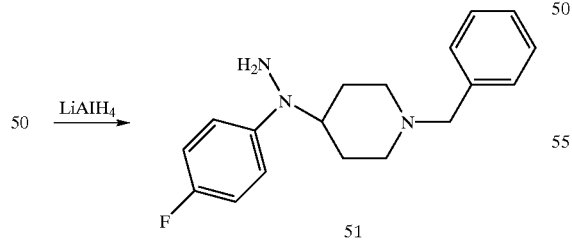

A dry THF solution (25 ml) of 50 (3.0 g, 9.6 mmol) was added, slowly, dropwise, under $N_2$ to a pre-cooled (ice bath) slurry of $LiAlH_4$ (0.76 g, 20 mmol) in dry THF (30 ml). After the addition, the mixture was allowed to warm up and was stirred at RT for 15 h. The mixture was then cooled again in an ice bath and the reaction was quenched by adding, dropwise under $N_2$, water (1.0 ml), then aqueous NaOH (1.0 ml of 15%), followed by 3.0 ml of water. The resulting solid was filtered through a pad of "Celite" and washed several times with THF. The reaction mixture was purified by flash chromatography on silica gel using 50% EtOAc/Hexanes as eluent. Yield: 1.95 g. (66%). MS: m/z= 300 (M+1).

Step 4:

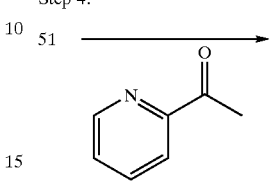

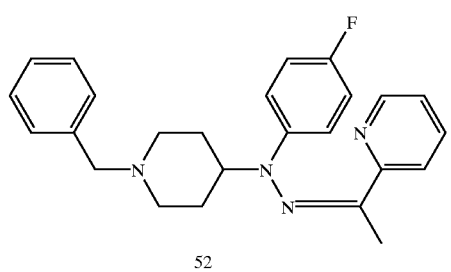

Neat 2-acetyl pyridine (0.73 g, 6.0 mmol) and 51 (1.0 g, 3.34 mmol) were heated in a pressure tube at a bath temperature of 140° C. for 19 h. The reaction mixture was purified by flash chromatography on silica gel using 20% EtOAc/Hexanes as eluent. Yield: 1.09 g. (81%). MS: m/z= 403 (M+1).

Step 5:

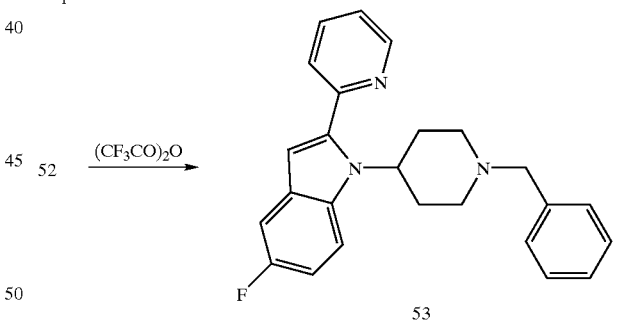

Trifluoroacetic anhydride (0.37 ml, 2.6 mmol) was added dropwise, under $N_2$, to a dry THF solution of 52 (0.816 g, 2.03 mmol) precooled in an ice bath. After the addition, the solution was stirred at 0° C. for 90 min, then heated to reflux for 5 h. After removing the solvent using reduced pressure, the residue was treated with saturated aqueous $NaHCO_3$ and extracted with $CH_2Cl_2$. The organic extracts were combined, washed with brine and dried over anhydrous $Na_2SO_4$. The reaction mixture was purified by flash chromatography on silica gel using 15% EtOAc/Hexanes as eluent. Yield: 0.56 g. (71%). MS: m/z=386 (M+1).

Step 6:

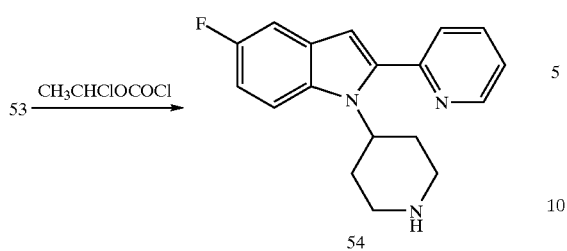

1-chloroethyl chloroformate (0.42 g, 3.9 mmol) was added, under $N_2$, at RT, to a solution of 53 (0.5 g, 1.3 mmol) dissolved in 1,2-dichloroethane (10 ml). The solution was then refluxed for 2 h, cooled to RT, $CH_3OH$ (5.0 ml) was added, and the solution refluxed again for 90 min. After removing the solvent with reduced pressure, the reaction mixture was purified by preparative TLC using 10% $CH_3OH$ ($NH_3$)/EtOAc as eluent. Yield: 0.23 g. (59%). MS: m/z=296 (M+1).

Step 7:

54 (92 mg, 1.58 mmol), Preparation 5 (113 mg, 0.47 mmol), EDC.HCl (0.105 mg, 0.55 mmol), and HOBT (74 mg, 0.55 mmol) were stirred at RT in dry DMF (2.0 ml) for 2 days. The reaction was quenched with 0.5 N aqueous NaOH (5.0 ml), then the solution was extracted with $CH_2Cl_2$. The combined extracts were washed with brine and dried over anhydrous $Na_2SO_4$. The title compound was isolated by preparative TLC on silica gel using EtOAc:Hexanes:$CH_3OH(NH_3)$ (70:25:5) as eluent. Yield: 82 mg. (51%). MS: m/z=513 (M+1).

Using a similar procedure, the following compounds were prepared:

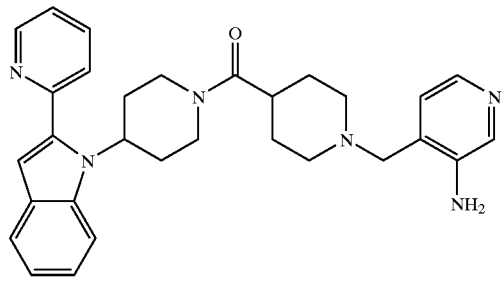

Ex. 19A: MS: m/z = 495 (M + 1).

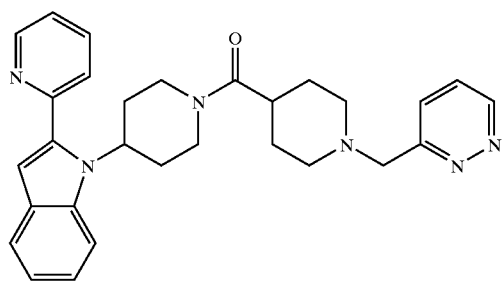

Ex. 19B: MS: m/z = 481 (M + 1).

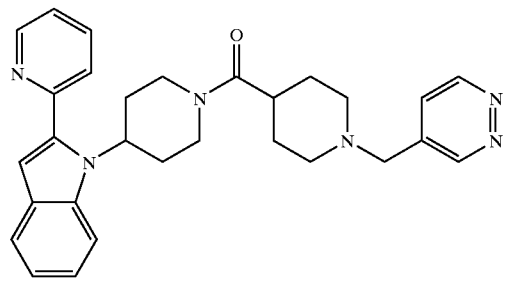

Ex. 19C: MS: m/z = 481 (M + 1).

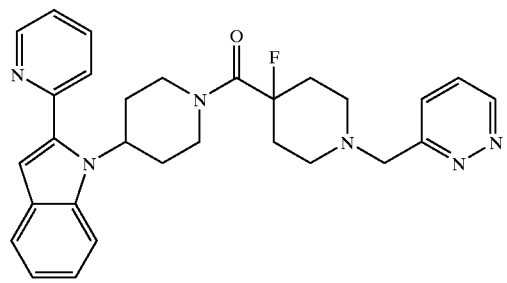

Ex. 19D: MS: m/z = 499 (M + 1).

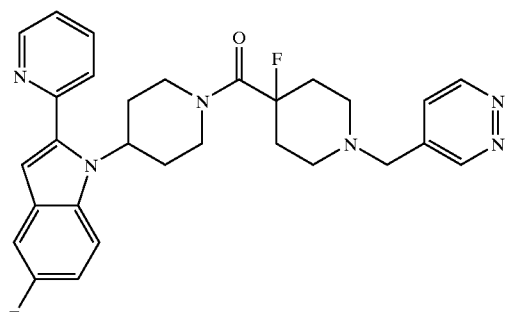

Ex. 19E: MS: m/z = 517 (M + 1).

Using the appropriate starting materials and the appropriate procedures shown above, the following compounds were made:

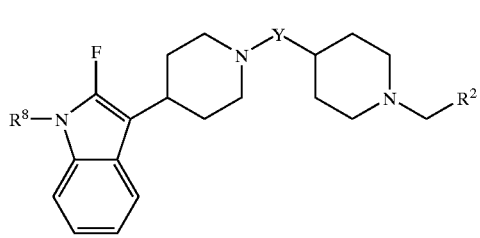

wherein R, $R^8$ and $R^2$ are as defined in the table:

| Ex. | R | R⁸ | Y | R² | Data MS (M + H) |
|---|---|---|---|---|---|
| 20 | phenyl | benzyl | —C(O)— | 4-(N-benzylamino)pyridin-2-yl | 674 |
| 21 | phenyl | 4-fluorobenzyl | —C(O)— | 4-(N-(4-fluorobenzyl)amino)pyridin-2-yl | 710 |
| 22 | phenyl | (1,2-dimethylimidazol-4-yl)sulfonyl | —C(O)— | 4-((1,2-dimethylimidazol-4-yl)sulfonylamino)pyridin-2-yl | 810 |
| 23 | phenyl | H | bond | 2-aminopyridin-4-yl | 466 |
| 24 | pyridin-2-yl | CH₃CH₂— | —C(O)— | 4-(N-ethylamino)pyridin-2-yl | 551 |
| 25 | pyridin-2-yl | (pyridin-2-yl)methyl | —C(O)— | 2-((pyridin-2-yl)methylamino)pyrimidin-5-yl | 678 |

-continued

| Ex. | R | R⁸ | Y | R² | Data MS (M + H) |
|---|---|---|---|---|---|
| 26 | 2-pyridyl | benzyl-CH | —C(O)— | pyrimidin-5-yl with 2-N(CH₂Ph)₂ | 766 |
| 27 | 2-pyridyl | pyrazin-2-yl | —C(O)— | 2-aminopyrimidin-5-yl | 574 |
| 28 | 2-pyridyl | piperidin-1-yl-(CH₂)₂— | —C(O)— | 2-aminopyrimidin-5-yl | 607 |
| 29 | 2-pyridyl | H | —C(O)— | imidazo[4,5-b]pyridin-7-yl | 520 |

EXAMPLE 30

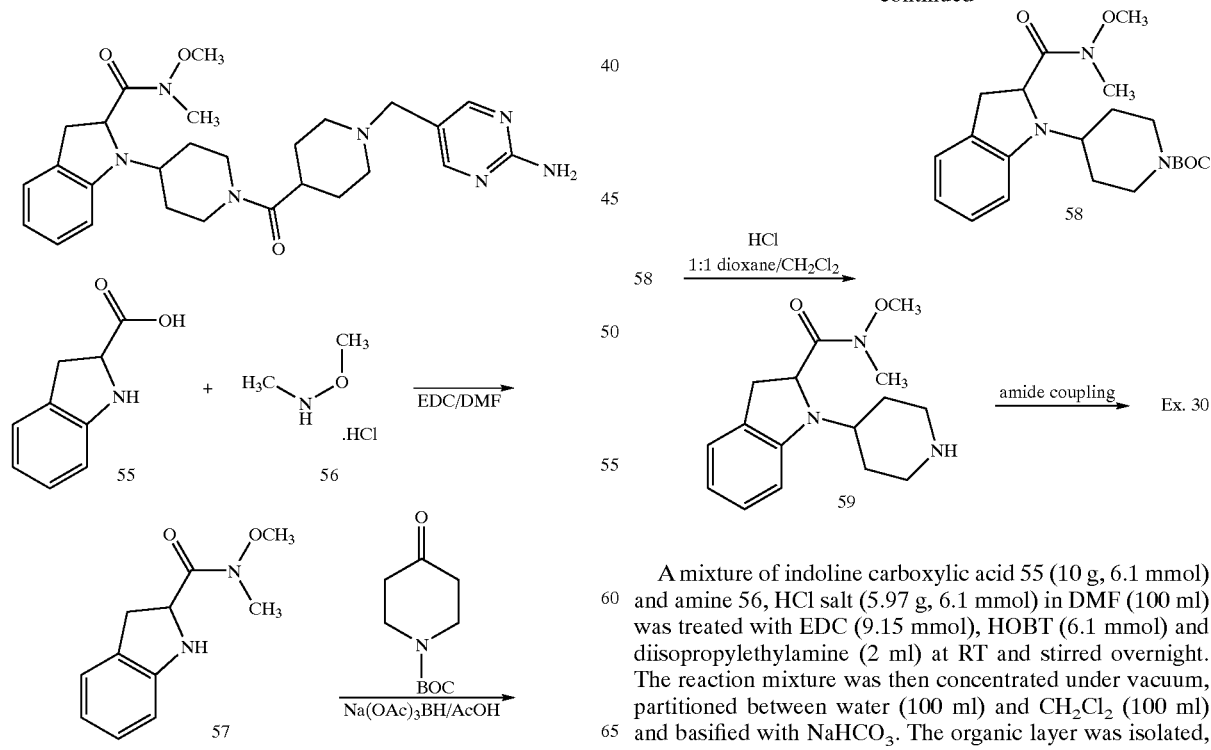

A mixture of indoline carboxylic acid 55 (10 g, 6.1 mmol) and amine 56, HCl salt (5.97 g, 6.1 mmol) in DMF (100 ml) was treated with EDC (9.15 mmol), HOBT (6.1 mmol) and diisopropylethylamine (2 ml) at RT and stirred overnight. The reaction mixture was then concentrated under vacuum, partitioned between water (100 ml) and CH₂Cl₂ (100 ml) and basified with NaHCO₃. The organic layer was isolated, dried and concentrated to provide crude 57. All of 57 was dissolved in AcOH (100 ml) and treated successively with BOC-piperidone (6.1 mmol) and Na(OAc)$_3$BH (12.2 mmol) and stirred at RT overnight. The reaction mixture was then partitioned between water (300 ml) and CH$_2$Cl$_2$ (200 ml) and basified with NaOH. The organic layer was isolated, washed with brine and dried with crystalline Na$_2$SO$_4$. Concentration under vacuum provided crude 58, quantitatively, as an off white solid. HCl cleavage of the BOC group provided 59. Using standard amide coupling techniques as described above, 59 was converted to the title compound. MS (M+1)=508.

Using the appropriate indolene starting materials in a similar procedure, the following compounds were prepared:

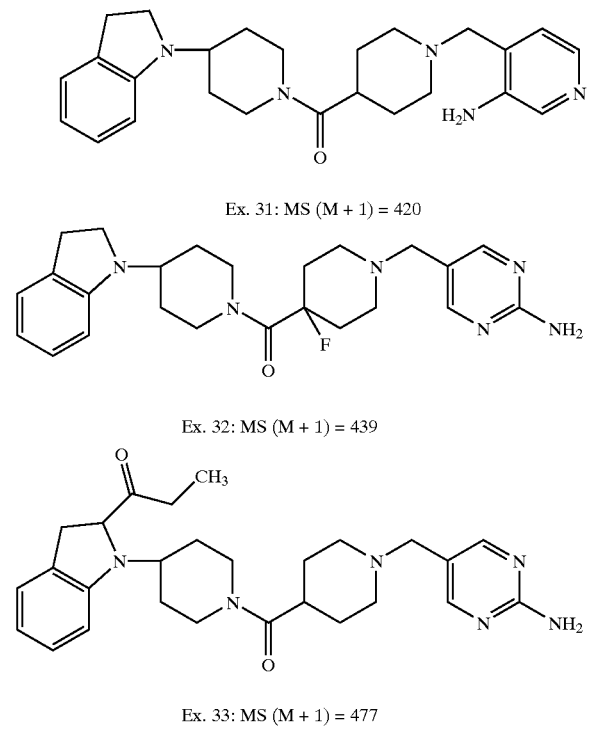

Ex. 31: MS (M + 1) = 420

Ex. 32: MS (M + 1) = 439

Ex. 33: MS (M + 1) = 477

General Procedure for H$_3$-Receptor Binding Assay

The source of the H$_3$ receptors in this experiment was guinea pig brain. The animals weighed 400–600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein) to the reaction tubes. The reaction was started by the addition of 3 nM [$^3$H]R-α-methyl histamine (8.8 Ci/mmol) or 3 nM [$^3$H]N$^\alpha$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a K$_i$ (nM).

Compounds of formula I have a K$_i$ within the range of about 1 to about 1000 nM. Preferred compounds of formula I have a K$_i$ within the range of about 1 to about 100 nM. More preferred compounds of formula I have a K$_i$ within the range of about 1 to about 20 nM. The compound of Example 5 has a Ki of 1.50 nM.

In this specification, the term "at least one compound of formula I" means that one to three different compounds of formula I may be used in a pharmaceutical composition or method of treatment. Preferably one compound of formula I is used. Similarly, "at least one H$_1$ receptor antagonist" means that one to three different H$_1$ antagonists may be used in a pharmaceutical composition or method of treatment. Preferably, one H$_1$ antagonist is used.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of $H_3$ antagonist and $H_1$ antagonist compounds, the two active components may be co-administered simultaneously or sequentially, or a single pharmaceutical composition comprising a $H_3$ antagonist and an $H_1$ antagonist in a pharmaceutically acceptable carrier can be administered. The components of the combination can be administered individually or together in any conventional dosage form such as capsule, tablet, powder, cachet, suspension, solution, suppository, nasal spray, etc. The dosage of the $H_1$ antagonist can be determined from published material, and may range from 1 to 1000 mg per dose. When used in combination, the dosage levels of the individual components are preferably lower than the recommended individual dosages because of the advantageous effect of the combination.

When separate $H_3$ and $H_1$ antagonist pharmaceutical compositions are to be administered, they can be provided in a kit comprising in a single package, one container comprising an $H_3$ antagonist in a pharmaceutically acceptable carrier, and a separate container comprising an $H_1$ antagonist in a pharmaceutically acceptable carrier, with the $H_3$ and $H_1$ antagonists being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula

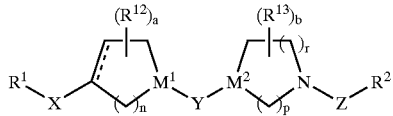

I or a pharmaceutically acceptable salt or solvate thereof, wherein:

a is 0 to 3;
b is 0 to 3;
n is 2;
p is 1, 2 or 3;
r is 0, 1, or 2;
X is a bond or $C_1$–$C_6$ alkylene;
$M^1$ is N;
$M^2$ is $C(R^3)$;
with the proviso that the sum of p and r is 3
Y is —C(=O)—, —C(=S)—, —(CH$_2$)$_q$—, —C(=O)NR$^4$—, —C(=O)CH$_2$—, —SO$_{1-2}$—, or —C(=N—CN)—NH—;
q is 1 to 5;
Z is a bond, $C_1$–$C_6$ alkylene, $C_2$–$C_6$ alkenylene, —C(=O)—, —CH(CN)— or —CH$_2$C(=O)NR$^4$—;

$R^1$ is

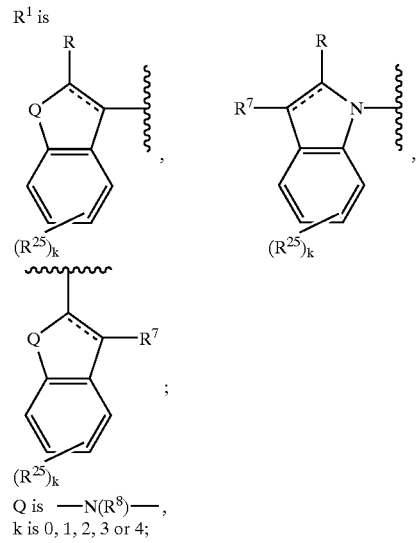

Q is —N(R$^8$)—,
k is 0, 1, 2, 3 or 4;

the dotted line represents an optional double bond;
R and R$^7$ are independently selected from the group consisting of H, $C_1$–$C_6$ alkyl, halo($C_1$–$C_6$)alkyl-, $C_1$–$C_6$ alkoxy, ($C_1$–$C_6$)alkoxy-($C_1$–$C_6$)alkyl-, ($C_1$–$C_6$)-alkoxy-($C_1$–$C_6$)alkoxy, ($C_1$–$C_6$)alkoxy-($C_1$–$C_6$)alkyl-SO$_{0-2}$, R$^{32}$-aryl($C_1$–$C_6$)alkoxy-, R$^{32}$-aryl-($C_1$–$C_6$) alkyl-, R$^{32}$-aryl, R$^{32}$-aryloxy, R$^{32}$-heteroaryl, ($C_3$–$C_6$) cycloalkyl, ($C_3$–$C_6$)cycloalkyl-($C_1$–$C_6$)alkyl, ($C_3$–$C_6$) cycloalkyl-($C_1$–$C_6$)alkoxy, ($C_3$–$C_6$)cycloalkyl-oxy-, R$^{37}$-heterocyclo-alkyl, N(R$^{30}$)(R$^{31}$)—($C_1$–$C_6$)alkyl-, —N(R$^{30}$)(R$^{31}$), —NH—($C_1$–$C_6$)alkyl-O—($C_1$–$C_6$) alkyl, —NHC(O)NH(R$^{29}$); R$^{22}$—S(O)$_{0-2}$—, ($C_1$–$C_6$)alkyl-S(O)$_{0-2}$—, N(R$^{30}$)(R$^{31}$)—($C_1$–$C_6$)alkyl-S(O)$_{0-2}$—, benzoyl, ($C_1$–$C_6$)alkoxy-carbonyl, R$^{37}$-heterocycloalkyl-N(R$^{29}$)—C(O)—, ($C_1$–$C_6$)alkyl-N (R$^{29}$)—C(O)—, ($C_1$–$C_6$)alkyl-N($C_1$–$C_6$ alkoxy)-C (O)—, —C(=NOR$^{36}$)R$^{36}$ and —NHC(O)R$^{29}$; and when the optional double bond is not present, R$^7$ can be OH;

R$^8$ is H, $C_1$–$C_6$ alkyl, halo($C_1$–$C_6$)alkyl-, ($C_1$–$C_6$)alkoxy-($C_2$–$C_6$)alkyl-, R$^{32}$-aryl($C_1$–$C_6$)alkyl-, R$^{32}$-aryl, R$^{32}$-heteroaryl, R$^{32}$-heteroaryl($C_1$–$C_6$)alkyl-, ($C_3$–$C_6$) cycloalkyl, ($C_3$–$C_6$)cycloalkyl-($C_1$–$C_6$)alkyl, R$^{37}$-heterocycloalkyl, R$^{37}$-heterocycloalkyl($C_1$–$C_6$)alkyl, N(R$^{30}$)(R$^{31}$)—($C_2$–$C_6$)alkyl-, R$^{22}$—S(O)$_2$—, halo ($C_1$–$C_6$)alkyl-S(O)$_2$—, R$^{22}$—S(O)$_{0-1}$—($C_2$–$C_6$)alkyl-, halo($C_1$–$C_6$)alkyl-S(O)$_{0-1}$—($C_2$–$C_6$)alkyl-, ($C_1$–$C_6$) alkyl-N(R$^{29}$)—SO$_2$—, or R$^{32}$-heteroaryl-SO$_2$;

R$^2$ is a six-membered heteroaryl ring having 1 or 2 heteroatoms independently selected from N or N—O, with the remaining ring atoms being carbon; a five-membered heteroaryl ring having 1, 2, 3 or 4 heteroatoms independently selected from N, O or S, with the remaining ring atoms being carbon; R$^{32}$-quinolyl; R$^{32}$-aryl;

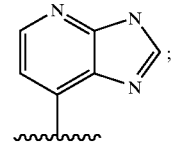

or heterocycloalkyl; wherein said six-membered heteroaryl ring or said five-membered heteroaryl ring is optionally substituted by R$^6$;

$R^3$ is H, halogen, $C_1$–$C_6$ alkyl, —OH or $(C_1$–$C_6)$alkoxy;

$R^4$ is independently selected from the group consisting of hydrogen, $C_1$–$C_6$ alkyl, $C_3$–$C_6$ cycloalkyl, $(C_3$–$C_6)$ cycloalkyl$(C_1$–$C_6)$alkyl, $R^{33}$-aryl, $R^{33}$-aryl$(C_1$–$C_6)$ alkyl, and $R^{32}$-heteroaryl;

$R^5$ is hydrogen, $C_1$–$C_6$ alkyl, —C(O)$R^{20}$, —C(O)$_2R^{20}$, —C(O)N$(R^{20})_2$, $R^{33}$-aryl$(C_1$–$C_6)$alkyl or $(C_1$–$C_6)$ alkyl-SO$_2$—;

$R^6$ is 1 to 3 substituents independently selected from the group consisting of —OH, halogen, $C_1$–$C_6$ alkyl, $C_1$–$C_6$ alkoxy, —CF$_3$, —NR$^4$R$^5$, —(C$_1$–C$_6$)alkyl-NR$^4$R$^5$, phenyl, $R^{33}$-phenyl, NO$_2$, —CO$_2$R$^4$, —CON$(R^4)_2$, —NHC(O)N$(R^4)_2$, $R^{32}$-heteroaryl-SO$_2$—NH—, $R^{32}$-aryl-(C$_1$–C$_6$)alkyl-NH—, $R^{32}$-heteroaryl-(C$_1$–C$_6$) alkyl-NH—, $R^{32}$-heteroaryl-NH—C(O)—NH—, $R^{37}$-heterocycloalkyl-N(R$^{29}$)—C(O)— and $R^{37}$-heterocycloalkyl-N(R$^{29}$)—C(O)—NH—;

$R^{12}$ is independently selected from the group consisting of $C_1$–$C_6$ alkyl, hydroxyl, $C_1$–$C_6$ alkoxy, or fluoro, provided that when $R^{12}$ is hydroxy or fluoro, then $R^{12}$ is not bound to a carbon adjacent to a nitrogen; or $R^{12}$ forms a $C_1$ to $C_2$ alkyl bridge from one ring carbon to another ring carbon;

$R^{13}$ is independently selected from the group consisting of $C_1$–$C_6$ alkyl, hydroxyl, $C_1$–$C_6$ alkoxy, or fluoro, provided that when $R^{13}$ is hydroxy or fluoro then $R^{13}$ is not bound to a carbon adjacent to a nitrogen; or forms a $C_1$ to $C_2$ alkyl bridge from one ring carbon to another ring carbon; or $R^{13}$ is =O;

$R^{20}$ is independently selected from the group consisting of hydrogen, $C_1$–$C_6$ alkyl, or aryl, wherein said aryl group is optionally substituted with from 1 to 3 groups independently selected from halogen, —CF$_3$, —OCF$_3$, hydroxyl, or methoxy; or when two $R^{20}$ groups are present, said two $R^{20}$ groups taken together with the nitrogen to which they are bound can form a five or six membered heterocyclic ring;

$R^{22}$ is $C_1$–$C_6$ alkyl, $R^{34}$-aryl or heterocycloalkyl;

$R^{24}$ is H, $C_1$–$C_6$ alkyl, —SO$_2$R$^{22}$ or $R^{34}$-aryl;

$R^{25}$ is independently selected from the group consisting of $C_1$–$C_6$ alkyl, halogen, CN, —CF$_3$, —OH, $C_1$–$C_6$ alkoxy, (C$_1$–C$_6$)alkyl-C(O)—, aryl-C(O)—, N(R$^4$)(R$^5$)—C(O)—, N(R$^4$)(R$^5$)—S(O)$_{1-2}$—, halo-(C$_1$–C$_6$) alkyl- or halo-(C$_1$–C$_6$)alkoxy-(C$_1$–C$_6$)alkyl-;

$R^{29}$ is H, $C_1$–$C_6$ alkyl, $R^{35}$-aryl or $R^{35}$-aryl(C$_1$–C$_6$)alkyl-;

$R^{30}$ is H, $C_1$–$C_6$ alkyl-, $R^{35}$-aryl or $R^{35}$-aryl(C$_1$–C$_6$) alkyl-;

$R^{31}$ is H, $C_1$–$C_6$ alkyl-, $R^{35}$-aryl, $R^{35}$-aryl(C$_1$–C$_6$)alkyl-, (C$_1$–C$_6$)alkyl-C(O)—, $R^{35}$-aryl-C(O)—, N(R$^4$)(R$^5$)—C(O)—, (C$_1$–C$_6$)alkyl-S(O)$_2$— or $R^{35}$-aryl-S(O)$_2$—;

or $R^{30}$ and $R^{31}$ together are —(CH$_2$)$_{4-5}$—, —(CH$_2$)$_2$—O—(CH$_2$)$_2$— or —(CH$_2$)$_2$—N(R$^{29}$)—(CH$_2$)$_2$— and form a ring with the nitrogen to which they are attached;

$R^{32}$ is 1 to 3 substituents independently selected from the group consisting of H, —OH, halogen, $C_1$–$C_6$ alkyl, $C_1$–$C_6$ alkoxy, $R^{35}$-aryl-O—, —SR$^{22}$, —CF$_3$, —OCF$_3$, —OCHF$_2$, —NR$^4$R$^5$, phenyl, $R^{33}$-phenyl, —NO$_2$, —CO$_2$R$^4$, —CON(R$^4$)$_2$, —S(O)$_2$R$^{22}$, —S(O)$_2$N(R$^{20}$)$_2$, —N(R$^{24}$)S(O)$_2$R$^{22}$, —CN, hydroxy-(C$_1$–C$_6$)alkyl-, —OCH$_2$CH$_2$OR$^{22}$, and $R^{35}$-aryl(C$_1$–C$_6$)-alkyl-O—, wherein said aryl group is optionally substituted with 1 to 3 independently selected halogens;

$R^{33}$ is 1 to 3 substituents independently selected from the group consisting of $C_1$–$C_6$ alkyl, halogen, —CN, —NO$_2$, —OCHF$_2$ and —O—(C$_1$–C$_6$)alkyl;

$R^{34}$ is 1 to 3 substituents independently selected from the group consisting of H, halogen, —CF$_3$, —OCF$_3$, —OH and —OCH$_3$;

$R^{35}$ is 1 to 3 substituents independently selected from the group consisting of hydrogen, halo, $C_1$–$C_6$ alkyl, hydroxy, $C_1$–$C_6$ alkoxy, phenoxy, —CF$_3$, —N(R$^{36}$)$_2$, —COOR$^{20}$ and —NO$_2$;

$R^{36}$ is independently selected from the group consisting of H and $C_1$–$C_6$ alkyl; and $R^{37}$ is independently selected from the group consisting of H, $C_1$–$C_6$ alkyl and (C$_1$–C$_6$)alkoxycarbonyl.

2. A compound of claim 1 wherein a is 0 and the optional double bond in the ring containing $M^1$ is not present.

3. A compound of claim 1 wherein $M^2$ is C(R$^3$) wherein $R^3$ is hydrogen or halogen, b is 0; r is 1 and p is 2.

4. A compound of claim 1 wherein Y is —C(O)—.

5. A compound of claim 1 wherein Z is straight or branched $C_1$–$C_3$ alkyl.

6. A compound of claim 1 wherein $R^2$ is a six-membered heteroaryl ring, optionally substituted with one $R^6$ substituent.

7. A compound of claim 6 wherein $R^2$ is pyridyl, pyrimidyl or pyridazinyl, optionally substituted with —NH$_2$.

8. A compound of claim 1 wherein $R^1$ is

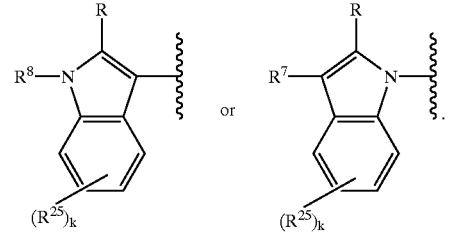

9. A compound of claim 8 wherein R is H, alkyl, $R^{32}$-aryl, $R^{32}$-heteroaryl, (C$_1$–C$_6$)alkoxy-carbonyl or (C$_1$–C$_6$)alkyl-N(R$^{29}$)—C(O)—.

10. A compound of claim 9 wherein R is $R^{32}$-phenyl or $R^{32}$-pyridyl.

11. A compound of claim 8 wherein $R^7$ is hydrogen.

12. A compound of claim 8 wherein $R^8$ is H, $R^{32}$-aryl (C$_1$–C$_6$)alkyl-, $R^{32}$-heteroaryl(C$_1$–C$_6$)alkyl-, $R^{32}$-aryl, $R^{32}$-heteroaryl, (C$_1$–C$_6$)alkyl-N(R$^{29}$)—S$_2$— or $R^{37}$-heterocycloalkyl(C$_1$–C$_6$)alkyl-.

13. A compound of claim 12 wherein $R^8$ is H, $R^{32}$-benzyl, $R^{32}$ pyridylmethyl, piperidinoethyl or (C$_1$–C$_6$)alkyl-N(R$^{29}$)—SO$_2$— wherein $R^{29}$ is H or $C_1$–$C_5$ alkyl.

14. A compound of claim 8 wherein $R^{25}$ is H, halogen or —CF$_3$ and k is 0 or 1.

15. A compound of claim 1 selected from the group consisting of compounds of the formula

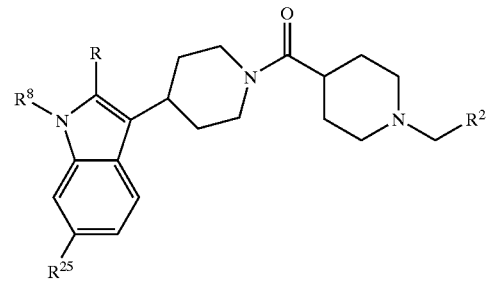

wherein R, $R^8$, $R^{25}$ and $R^2$ are as defined in the table:

| R | $R^8$ | $R^{25}$ | $R^2$ |
|---|---|---|---|
| phenyl | $(CH_3)_2N-SO_2-$ | H | 2-aminopyridin-4-yl |
| pyridin-2-yl | pyridin-2-ylmethyl | H | 2-aminopyridin-4-yl |
| $CH_3CH_2-O-C(O)-$ | H | H | 2-aminopyridin-4-yl |
| $CH_3-NH-C(O)-$ | H | H | 2-aminopyridin-4-yl |
| pyridin-2-yl | H | H | 2-aminopyridin-4-yl |

-continued

| R | $R^8$ | $R^{25}$ | $R^2$ |
|---|---|---|---|
| pyridin-2-yl | H | F | 2-aminopyridin-4-yl |
| pyridin-2-yl | 2-(piperidin-1-yl)ethyl | H | 2-aminopyridin-4-yl |
| pyridin-2-yl | 2-(piperidin-1-yl)ethyl | H | 2-aminopyrimidin-5-yl |

16. A pharmaceutical composition comprising an effective amount of a compound of claim 1 and a pharmaceutically effective carrier.

17. A method of treating congestion comprising administering to a patient in need of such treatment an effective amount of a compound of claim 1.

* * * * *